United States Patent [19]

Merrill, Jr. et al.

[11] Patent Number: 5,232,837

[45] Date of Patent: Aug. 3, 1993

[54] METHOD OF ALTERING SPHINGOLIPID METABOLISM AND DETECTING FUMONISIN INGESTION AND CONTAMINATION

[75] Inventors: Alfred H. Merrill, Jr., Stone Mountain; Elaine W. Wang, Atlanta; Ronald T. Riley, Athens, all of Ga.

[73] Assignees: Emory University, Atlanta, Ga.; The United States of America as represented by the Secretary of Agriculture, Washington, D.C.

[21] Appl. No.: 740,426

[22] Filed: Aug. 5, 1991

[51] Int. Cl.$^5$ .............................................. C12Q 1/48
[52] U.S. Cl. ........................................ 435/15; 436/20; 436/63; 436/64; 436/71; 436/815; 560/196; 564/507
[58] Field of Search ...................... 436/63, 64, 71, 815; 435/15, 16

[56] References Cited

U.S. PATENT DOCUMENTS 5,103,002  4/1992  Wieland .............................. 564/224

OTHER PUBLICATIONS

Merrill et al., *Anal. Biochem.*, vol. 171, pp. 373-381 (1988).

Wang, et al., "Inhibition of Sphingosine Biosynthesis by Fumonisins, Mycotoxins Produced by *Fusarium Moniliforme, Environmental Pathology and Toxicology*" 7164-7165 (1991), abstract presented at Federation of American Societies for Experimental Biology, Atlanta, Ga., Apr., 1991.

Merrill, Alfred H., Jr., "Cell Regulation by Sphingosine and More Complex Sphingolipids," *Journal of Bioenergetics and Biomembranes* 23:83-104 (1991).

"Fumonisins: A Current Perspective View and a View to the Future," various papers on fumonisins presented at a meeting (Apr. 1991).

Norred et al., "In Vitro Toxicology of Fumonisin and *F. moniliforme* Toxins and the Mechanistic Implications," presented at Fumonisins: A Current Perspective and a View to the Future, meeting (Apr. 1991).

Bottini, et al., "Characterization of a Phytotoxic Fraction from *Alternaria Alternate F. SP. Lycopersici,*" *Tetrahedron Letters* 22:2723-2726 (1981).

*Primary Examiner*—Richard L. Raymond
*Assistant Examiner*—Scott C. Rand
*Attorney, Agent, or Firm*—Needle & Rosenberg

[57] ABSTRACT

This invention provides a method of altering the metabolism of sphingolipids in a cell comprising contacting the cell with a fumonisin, or an analog thereof. The invention also provides a method of detecting the consumption of a fumonisin or a fumonisin analog in a subject comprising (A) detecting, in a sample from the subject, the state of the metabolic pathway of sphingolipids and (B) comparing the state of the metabolic pathway to that of a normal subject, the presence of a change in the state of the metabolic pathway indicating the consumption of a fumonisin or a fumonisin analog. Also provided is a method of detecting the presence of a fumonisin or fumonisin analog contamination in a sample from a food or feed comprising detecting a reaction of the metabolic pathway of sphingolipids, the presence of the reaction indicating the presence of a fumonisin or fumonisin analog contamination. Furthermore, novel fumonisin analogs and compositions comprising fumonisins and fumonisin analogs are provided.

9 Claims, 20 Drawing Sheets

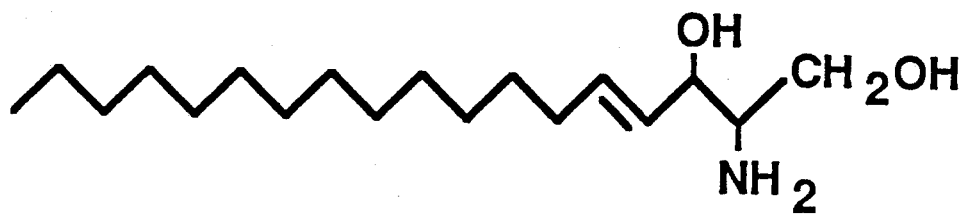
Sphingosine
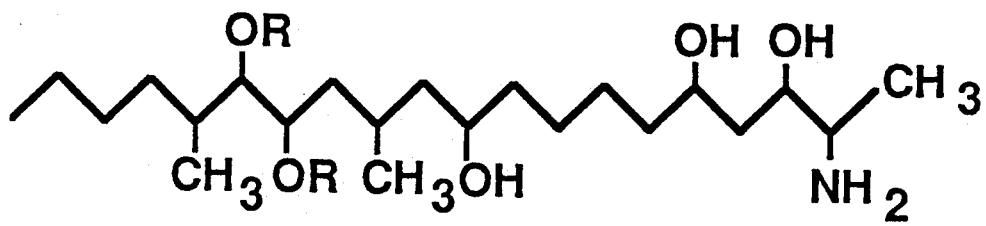
Fumonisin B$_1$
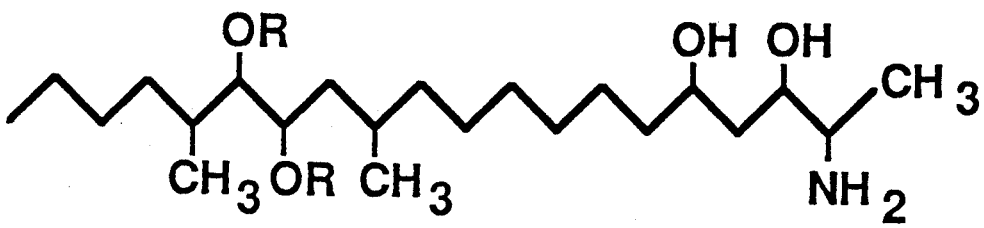
Fumonisin B$_2$
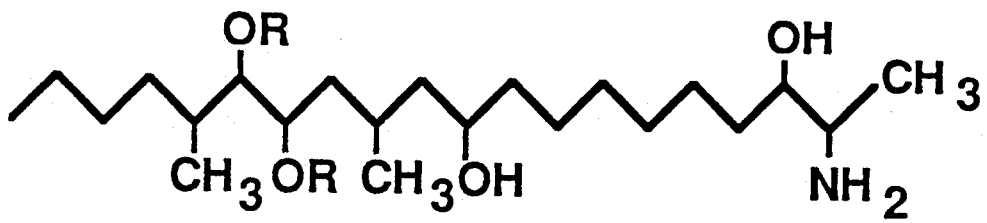
Fumon

Fumonisin B₄

Alternaria toxins (AAL toxins)

$R_1$ = H or R'

R = COCH$_2$CH(COOH)CH$_2$COOH

Fumonisin Analogs

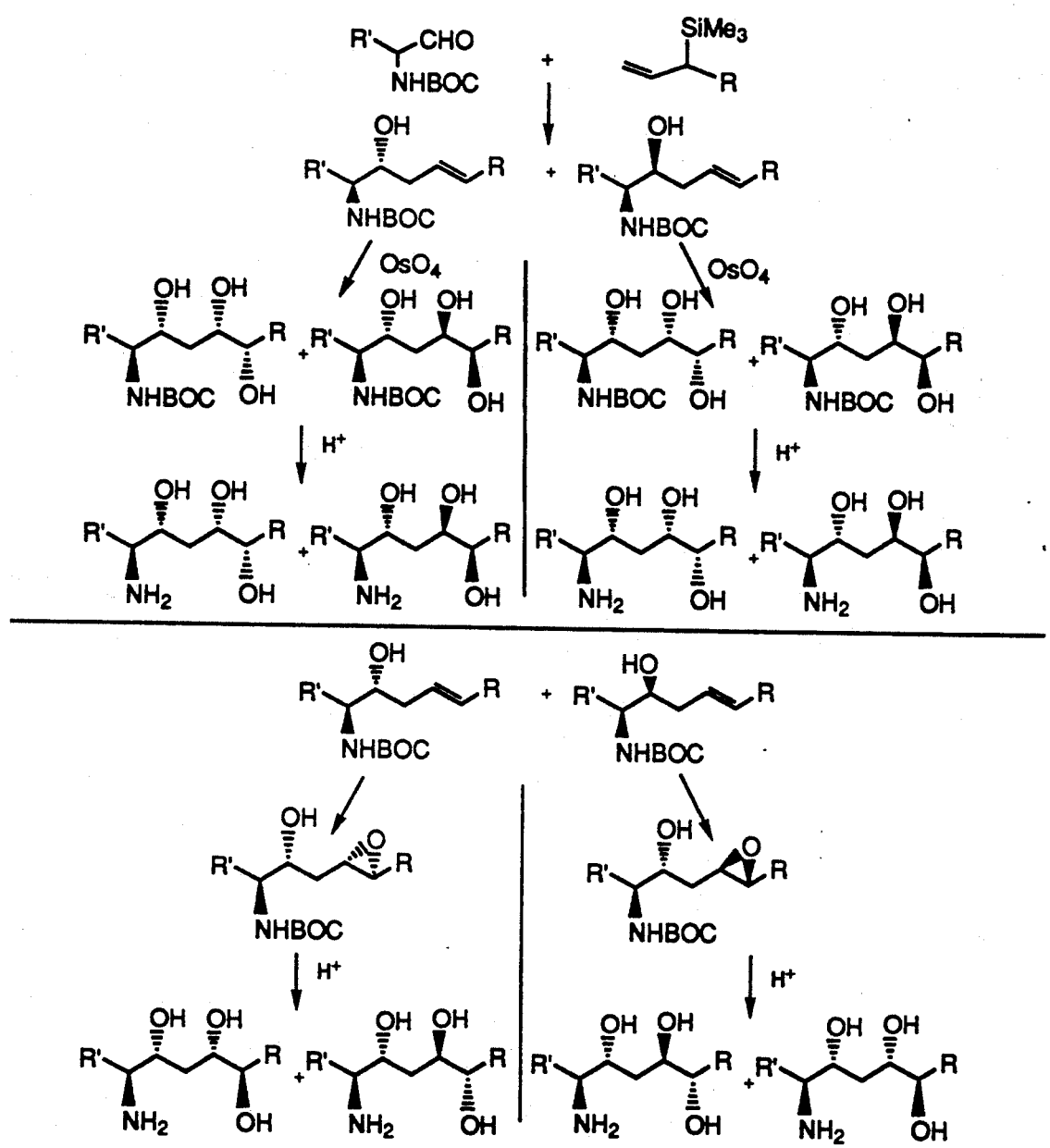

R = alkyl (straight chain or branched, $C_8$ - $C_{20}$), hydroxy alkyl, amino alkyl, alkylcarboxy (same definition of alkyl), aryl, esters of the hydroxyalkyl and alkylcarboxy groups, amides of the aminoalkyl and alkylcarboxy groups.
R' = H, $CH_3$, $C_2H_5$, $CH_2O$-Protecting Group Epoxide opening and removal of the BOC group may be more efficiently achieved using two discrete hydrolysis steps.

Figure 11

METHOD OF ALTERING SPHINGOLIPID METABOLISM AND DETECTING FUMONISIN INGESTION AND CONTAMINATION

The following invention was made through support from grant number GM 33369 from the National Institutes of Health, grant number DCB 8710283 from the National Science Foundation and grant number CRIS 6612-42000-004 to the United States Department of Agriculture. The United States government has rights in the invention.

Throughout this application, various publications are referenced. The full citation of these publications is provided in a bibliography immediately before the claims. The disclosures of these publications are hereby incorporated by reference to more fully describe the state of the art at the time the invention was made.

BACKGROUND OF THE INVENTION

*Fusarium moniliforme* (Sheldon) is one of the most prevalent fungi on maize, other grains, and agricultural commodities in the United States and throughout the world (1). Culture materials from certain isolates of (and grains naturally contaminated with) *F. moniliforme* have been shown to be toxic and carcinogenic for animals (2-5); furthermore, consumption of contaminated maize has been correlated with esophageal cancer in areas of southern Africa, China, and other countries (6-8). Several mycotoxins, termed fumonisins, have been isolated from extracts of *F. moniliforme* (9) and naturally contaminated corn (10,11). Fumonisin $B_1$ has been shown to cause equine leucoencephalomalacia (12), porcine pulmonary edema (13), and promotion of liver tumors in rats (14). Recent surveys indicate that high levels of fumonisin $B_1$ are present on United States feeds associated with field cases of these animal diseases (15).

The molecular mechanism of action of the fumonisins is not known. However, this invention provides the discovery that these compounds bear a remarkable structural similarity to sphingosine, the long-chain (sphingoid) base backbone of sphingomyelin, cerebrosides, sulfatides, gangliosides and other sphingolipids. Sphingolipids are thought to be involved with the regulation of cell growth, differentiation, and neoplastic transformation through participation in cell-cell communication and cell-substratum interactions, and possible interactions with cell receptors and signalling systems (16-20). This invention provides that fumonisins and fumonisin analogs target the disruption of sphingosine metabolism and that fumonisins and fumonisin analogs inhibit de novo sphingolipid biosynthesis in animals. This invention further identifies the reactions catalyzed by ceramide synthase as important sites for altering sphingolipid metabolism. This core discovery of the biochemical action of fumonisins provides a means to treat the many diseases associated with sphingolipid metabolism as well as a means for early detection of fumonisin contamination or ingestion.

SUMMARY OF THE INVENTION

This invention provides a method of altering the metabolism of sphingolipids in a cell, comprising contacting the cell with a fumonisin or an analog thereof. Also provided is a method of treating an abnormal condition in a subject associated with an alteration in sphingolipid metabolism comprising administering a fumonisin, or an analog thereof, to the subject in a metabolism altering amount. In addition, a composition comprising a fumonisin, or an analog thereof, in a pharmaceutically acceptable carrier is provided. As used herein "a fumonisin" only includes those fumonisins with the metabolism altering activity.

Also provided is a method of treating an abnormal condition in a subject associated with the ingestion of a fumonisin, or an analog thereof, which results in the depletion of a sphingolipid in the subject, comprising adding an amount of the sphingolipid to the subject sufficient to treat the condition. Further provided is a method of treating an abnormal condition in a subject associated with the ingestion of a fumonisin, or an analog thereof, which results in the accumulation of a sphingolipid, comprising adding an amount of an inhibitor of the sphingolipid to the subject sufficient to treat the condition.

The invention also provides a method of detecting the consumption of a fumonisin, or an analog thereof, in a subject comprising (A) detecting, in a sample from the subject, the state of the metabolic pathway of sphingolipids and (B) comparing the state of the metabolic pathway to that of a normal subject, the presence of a change in the state of the metabolic pathway indicating the consumption of a fumonisin or a fumonisin analog. Also provided is a method of detecting the presence of a fumonisin or fumonisin analog contamination in a sample from a food or feed comprising detecting a reaction in the metabolic pathway of sphingolipids, the presence of the reaction indicating the presence of a fumonisin or fumonisin analog contamination.

Furthermore, the invention provides a method of diagnosing an abnormal condition in a subject associated with an alteration in sphingolipid metabolism comprising detecting the state of the metabolic pathway of sphingolipids in a subject and comparing the state of the metabolic pathway to that of a normal subject, the presence of a change in the state of the metabolic pathway indicating the presence of an abnormal condition.

Finally, this invention provides for novel fumonisin analogs and compositions comprising fumonisins and fumonisin analogs.

BRIEF DESCRIPTION OF THE FIGURES

FIG. 1. shows structures of sphingosine, Alternaria toxins, fumonisin analogs and fumonisins $B_1$ and $B_2$.

FIG. 11 shows various reaction schemes that can be employed to control the stereochemistry of the aminotriol head groups present in Alternaria toxins or fumonisin analogs similar to Alternaria toxins.

DETAILED DESCRIPTION OF THE INVENTION

This invention provides the core discovery that fumonisins, and their analogs, affect the biosynthetic pathway of sphingolipids. Fumonisins and their analogs are generally referred to collectively as "fumonisin" or "fumonisins" herein. However, analogs may also be specifically addressed at various times in the specification. "Purified fumonisin" means a fumonisin separated from at least some contaminants associated with fumonisins occurring in nature.

Thus, the present invention provides a method of altering the metabolism of sphingolipids in a cell comprising contacting the cell with a metabolism altering amount of a fumonisin, or an analog thereof. In determining the precise mechanism through which fumonisins act, it has been discovered that the alteration in metabolism is effected by the fumonisin, or an analog thereof, binding to ceramide synthase in the conversion of sphinganine to dihydroceramide. Additionally, the invention provides that the alteration in metabolism can be effected by fumonisin, or an analog thereof, binding to ceramide synthase in the conversion of sphingosine back to ceramide. However, the fumonisins could act on various other aspects of the sphingolipid biosynthetic pathway and thus are not limited by the particular pathway so long as sphingolipid metabolism is altered.

As used herein, "ceramide synthase" means an enzyme or enzymes which add in N-acyl linkage to sphingosine, sphinganine and other long-chain bases. Thus, both sphinganine N-acyltransferase, which catalyzes the conversion of sphinganine to dihydroceramide, and sphingosine N-acyltransferase, which catalyzes the conversion of sphingosine to ceramide, are referred to as ceramide synthase herein. As also used herein, "analog of dihydroceramide or ceramide" means a compound which can be catalyzed by a fumonisin or an analog.

Figure 9:
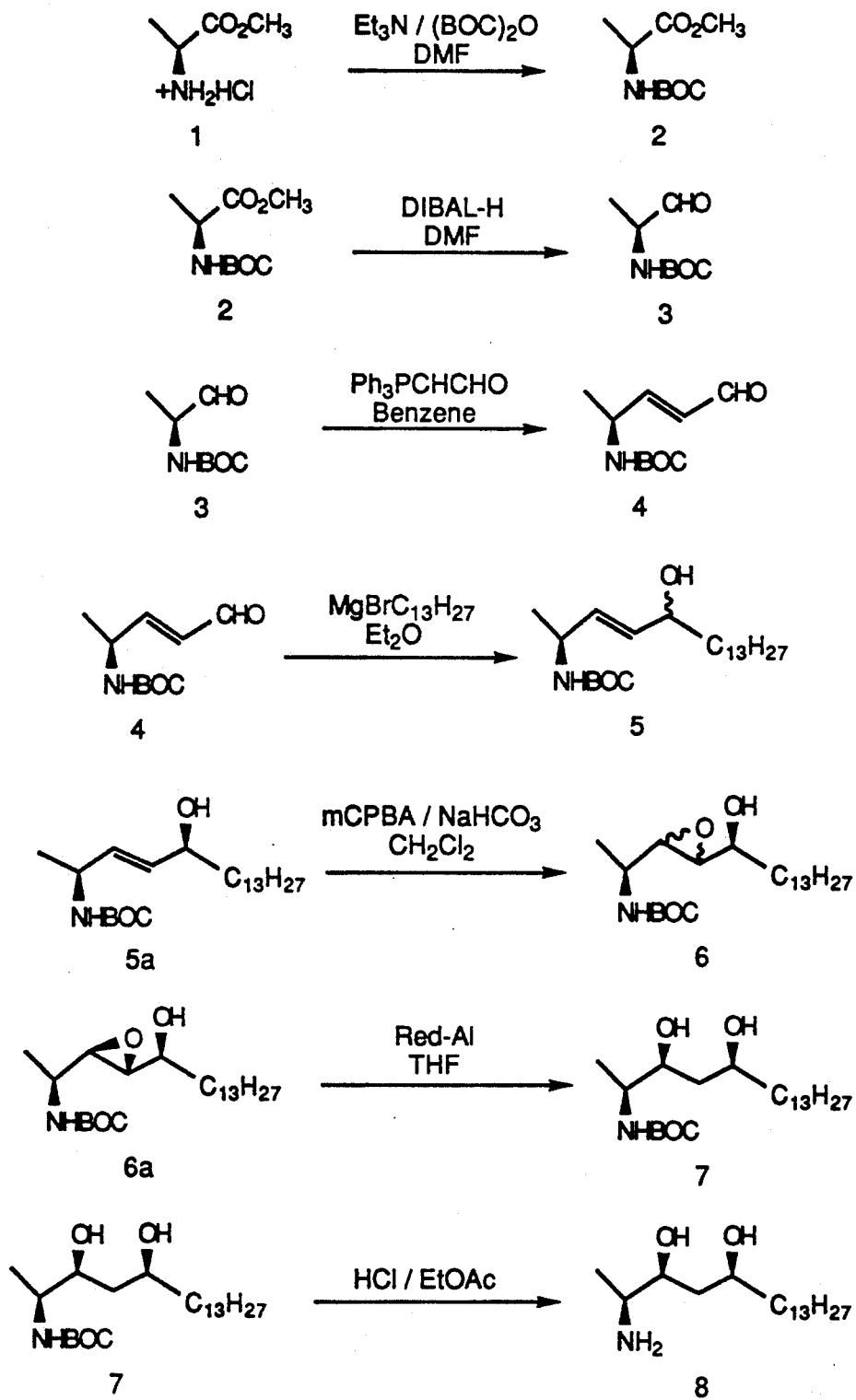
FIG. 9 shows the synthesis of a fumonisin analog.
Figure 10:
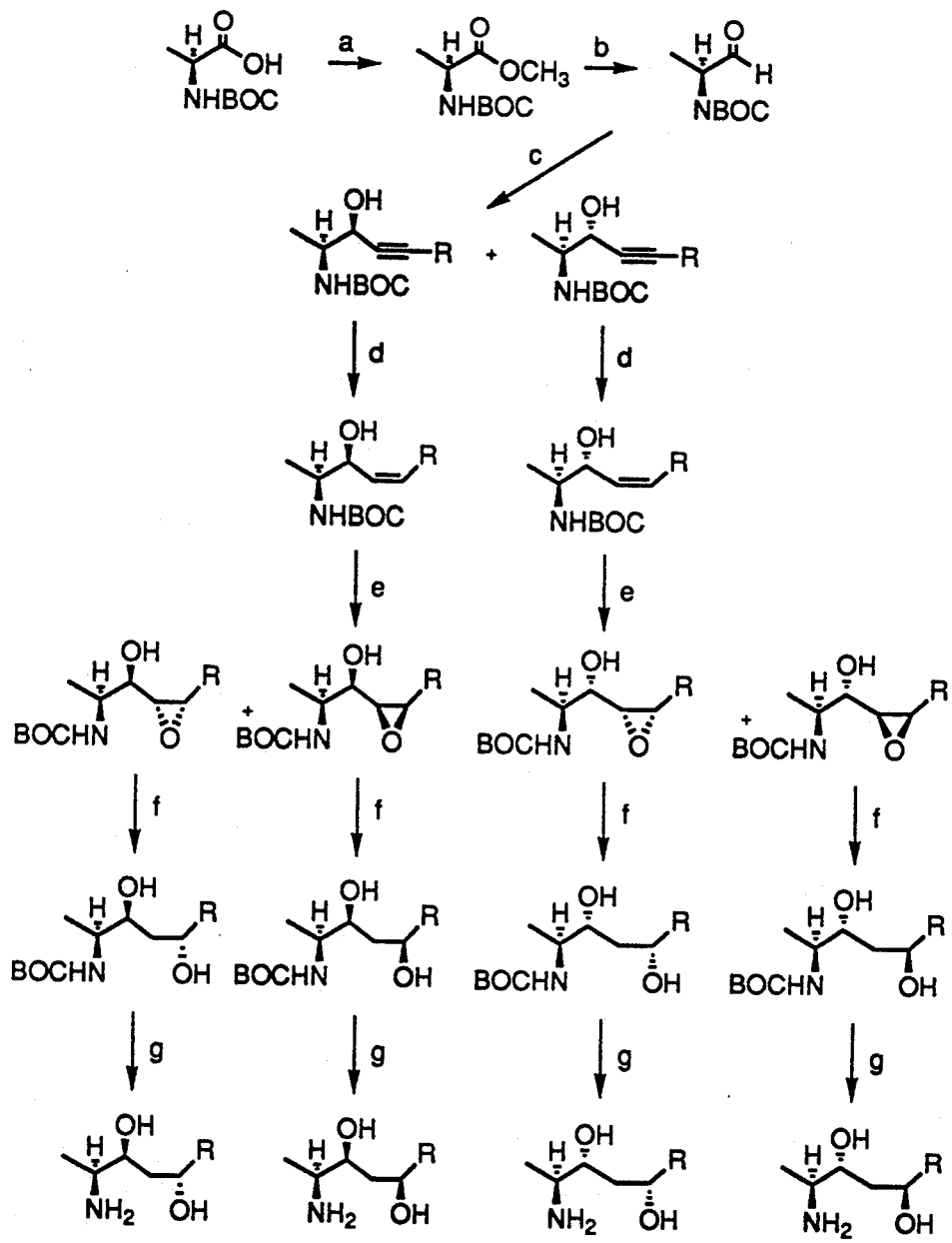
FIG. 10 shows reaction schemes which can be employed to control the stereochemistry of the 2-aminopenta-3,5-diol head group during the synthesis of a fumonisin analog.

This invention demonstrates that fumonisins can alter the metabolism of sphingolipids. The invention provides the discovery that fumonisins have a structure similar to sphingosine. Thus, the activity of the fumonisins likely relates to this structural similarity. In this regard, the fumonisins and sphingosine share a 2-amino-3-ol head group and possess backbone carbon chains of approximately equal size. However, sphingosine is hydroxyl-substituted at carbon 1 while fumonisin $B_1$ and $B_2$ are hydroxyl-substituted at carbon 5. In addition, the fumonisins possess polycarboxylate moieties attached to the tail of the backbone carbon chain. Thus, these similarities and differences between sphingosine in their head groups and tails are responsible for the activity of the fumonisins. Moreover, one merely needs to make various analogs based on these principles and test the analogs to determine if they have sphingolipid metabolism affecting activity. Such making can be done using techniques set forth herein. Modifications on these techniques to obtain additional analogs would be standard. Likewise, these compounds, once synthesized, could be tested for activity using the methods set forth below Thus, "fumonisin analog" as used herein is given a function as well as structural definition. "Fumonisin analog" means any compound which has structural similarity to fumonisin $B_1$, $B_2$, $B_3$ or $B_4$ and can alter the metabolism of sphingolipids. By structural similarity to a fumonisin, we mean analogs comprised of three basic units as given in FIG. 1: (a) a 1-aminobutan-2-ol head group which may be further substituted by substituents X, Y and IV; (b) a Spacer Group consisting of an alkyl, hydroxyalkyl or dihydroxyalkyl chain (straight or branched); (c) a hydrophilic tail (Z-W) in which Z contains an oxygen or nitrogen atom which can be further functionalized to attach mono- or polycarboxylate moieties (W). In this structure, the Spacer Group=alkyl, hydroxyalkyl or dihydroxyalkyl (straight chain or branched, $C_1$-$C_{20}$); Z=H, O, NH, NQ, NQC(O), NHC(O), $CO_2$, C(O)NH, C(O)NQ, wherein Q is an alkyl (straight chain or branched, $C_1$-$C_6$); W=no substituent, H, alkyl (straight chain or branched, $C_1$-$C_6$), aryl (phenyl, substituted phenyl such as substitution with alkyl (straight chain or branched, $C_1$-$C_6$) or halo), $C(O)(CH_2)_nCO_2H$ (where n=1-6), $C(O)(CH_2)_nCW'_2CO_2H$, where W' is selected independently from H, alkyl (straight chain or branched, $C_1$-$C_6$), aryl (phenyl, substituted phenyl such as substitution with alkyl (straight chain or branched, $C_1$-$C_6$) or halo), $(CH_2)_nCO_2H$ and $n=1-6$; $X=H$, methyl, $CH_2OH$ (and esters thereof), $CH_2NQ'_2$ (where $Q'$ is selected independently from H, alkyl (straight chain or branched, $C_1-C_{20}$), acyl ($C(O)Q''$ where $Q''$ is an alkyl, straight chain or branched, $C_1-C_{20}$)); and V and $Y=H$ or OH (and esters thereof). Also, explicitly included in the term "fumonisin analog" are the Alternaria toxins (AAL, toxins) as given in FIG. 1 and discussed in reference 33 and, by inference, similar compounds produced by other plants and fungi. Specific structures of various analogs and general synthesis methods are set forth below and in FIGS. 1, 9 and 10.

"Altering the metabolism" as used herein means either an increase or a decrease in the concentration of compounds formed in the sphingolipid biosynthetic pathway depending on what point in the pathway is affected. Typically, since ceramide synthase (sphinganine-N-acyltransferase) is generally bound by the fumonisin or fumonisin analog, and ceramide synthase (sphinganine-N-acyltransferase), which can also be bound by fumonisins, catalyzes the conversion of sphinganine to dihydroceramide in the pathway, the concentration of any compound above the site of action can be increased and the concentration of any compound below the site of action can be decreased using the fumonisin or fumonisin analog. However, the amounts of various compounds of the pathway can depend on the time period after inhibition or their relationship to other related pathways. For example, a fumonisin can bind sphingosine-N-acyltransferase, which would increase the amount of sphingosine by preventing the conversion back to ceramide and a fumonisin can also bind ceramide synthase (sphinganine-N-acyltransferase), which would decrease the amount of sphingosine by decreasing the amount of ceramide which can be converted to sphingosine. Thus, the fumonisin can cause both the increase and/or decrease of sphingosine, depending on which pathway is dominant. Such increases or decreases at various times after fumonisin ingestion can be routinely determined by methods utilized herein.

"Contacting the cell" as used herein means the fumonisin is administered in such a way that the fumonisin can enter the cell and affect the sphingolipid biosynthetic pathway within the cell. As shown below, the cell can be in a human or a nonhuman animal. Such in vivo activity is not only shown, but would be expected, because the nature of the sphingolipid metabolism would not differ fundamentally in vivo.

"Metabolism altering amount" as used herein means a quantity of a fumonisin capable of effecting a change in the sphingolipid metabolism in cells. Naturally, this amount can vary depending on the environment in which the cells are contained. For in vivo administration, the precise quantity of the fumonisin to elicit the desired effect can be determined by standard administration and monitoring until optimal dosage is determined. Such amounts can vary from subject to subject depending on size and condition of the subject.

As discussed above, the invention also provides a method of treating an abnormal condition in a subject associated with an alteration in sphingolipid metabolism. This method comprises administering a fumonisin, or an analog thereof, to the subject in a metabolism altering amount. The subject can be a human or a nonhuman animal and the abnormal condition can be caused by numerous disorders in sphingolipid metabolism. For example, the condition can be an excess of sphingosine resulting in Neimann-Picks syndrome, Tay-Sachs disease, a neoplastic condition or toxicity. In a given condition, the effects of fumonisin may be complex. For example, in a neoplastic condition, the fumonisin can, due to its structural similarity to sphingosine, prevent the formation of a sphingolipid required for growth of the cells and can also act as an inducer of differentiation and thus treat the neoplastic condition.

The invention also provides a method of treating an abnormal condition in a subject associated with the ingestion of a fumonisin or fumonisin analog which results in the depletion of a sphingolipid in the subject. This method comprises adding an amount of the sphingolipid to the subject sufficient to treat the condition. As can be seen by the pathway set forth in the figures, in general, compounds that occur in the biochemical pathway of sphingolipids after sphinganine can be depleted if sphinganine is not converted to dihydroceramide due to a fumonisin. Thus, adding the depleted compound or alternate compounds bypasses the blocked step. Similarly, fumonisins can bind ceramide synthase to prevent the conversion of sphingosine to ceramide and lead to an increase in sphingosine or a decrease in ceramide. Thus, adding the depleted compound or alternate compounds can also bypass this blocked step. Such conditions which can be effectively treated by this method can be determined by administering the compound to subjects suspected of suffering such conditions. Likewise, an administration regimen can be optimized by routine testing.

Also provided is a method of treating an abnormal condition in a subject associated with the ingestion of a fumonisin or a fumonisin analog which results in the accumulation of a sphingolipid comprising adding an amount of an inhibitor of the sphingolipid to the subject sufficient to treat the condition. This method can be effective since compounds prior to dihydroceramide, especially sphinganine, can accumulate if sphinganine is not converted to dihydroceramide. Likewise, compounds such as sphingosine can accumulate if sphingosine is not converted to ceramide. Regimens can be determined as discussed above.

In treating an abnormal condition, the amount of fumonisin, or an analog thereof, which is administered can vary. Preferably the amount is between about 5 and 500 mg, especially between about 25 and 75 mg when fumonisin $B_1$ or $B_2$ is utilized or an analog with a similar activity. The compounds according to the present invention are included in the pharmaceutically acceptable carrier in an amount sufficient to exert a therapeutically useful effect without exhibiting adverse toxic effects on the patient treated. Pharmaceutically compatible binding agents and/or adjuvant materials may also be included as part of the composition. The active materials can also be mixed with other active materials that do not impair the desired action and/or supplement the desired action. In general, the ratio of the fumonisin or the analog to the carrier is determined by the rate of administration and can be optimized using routine procedures.

It will be appreciated by those skilled in the art that the effective amount of a compound or formulation containing the compound required to treat an individual will vary depending on a number of factors, including whether the fumonisin or the analog is administered, the route of administration, the nature of the condition being treated and the age and condition of the patient. The desired dose may be given in a single dose or as divided doses administered at appropriate intervals, such as two, three, four or more sub-doses per day. Thus, these compounds or their pharmaceutically acceptable derivatives can be conveniently administered by a convenient route of administration, such as parenteral, including intramuscular, subcutaneous and intravenous; oral; rectal; nasal; vaginal or by inhalation.

The invention also provides a composition comprising a fumonisin, or an analog thereof, in a pharmaceutically acceptable carrier. The carrier can be any carrier suitable for administration to a subject, for example, buffered saline. The fumonisin, or an analog thereof, can be present in an amount between 5 and 500 mg. Especially effective is an amount between 25 and 75 mg.

The invention also provides a method of detecting the consumption of a fumonisin or a fumonisin analog in a subject comprising (A) detecting, in a sample from the subject, the state of the metabolic pathway of sphingolipids and (B) comparing the state of the biosynthetic pathway to that of a normal subject, the presence of a change in the state of the biosynthetic pathway indicating the consumption of a fumonisin. The change in the metabolic pathway can, for example, be an increase in sphinganine or a decrease in a compound following sphinganine in the pathway or an increase in sphingosine. The discovery of the fact that fumonisins act on the sphingolipid biosynthetic pathway allows for easy diagnostics to be established based on pathway changes in a subject such as a horse or a human. This method provides a means to constantly monitor humans or valuable farm animals to detect fumonisin or fumonisin analog intake, such as AAL toxins, before the fumonisin or analog causes a lethal effect.

A method of detecting the presence of a fumonisin or fumonisin analog contamination in a sample from a food or feed is also provided. The method comprises detecting a reaction of the metabolic pathway of sphingolipids, the presence of the reaction indicating the presence of a fumonisin contamination. For example, the reaction can be the prevention of the conversion of sphinganine, or an analog thereof, to dihydroceramide or an analog thereof, or the conversion of sphingosine, or an analog thereof, to ceramide, or an analog thereof, by ceramide synthase. However, again based on the core knowledge of the effect of a fumonisin on sphingolipid biosynthesis, related means of detecting the fumonisin can be established. The invention also provides a method of detecting the presence of a fumonisin contamination in a sample from a food comprising detecting a reaction of the metabolic pathway of sphingolipids, the presence of the reaction indicating the presence of fumonisin contamination. For example, the reaction is the conversion of sphingosine to ceramide or an analog thereof by ceramide synthase.

Finally, the invention provides a method of diagnosing an abnormal condition in a subject associated with an alteration in sphingolipid metabolism comprising detecting the state of the metabolic pathway of sphingolipids in a subject and comparing the state of the metabolic pathway to that of a normal subject, the presence of a change in the state of the metabolic pathway indicating the presence of an abnormal condition. For example, an increase in sphinganine can indicate increased risk of esophageal cancer. Such a change can be detected by the following methods listed below, and abnormal conditions other than esophageal cancer can be determined by using such methods. The conditions can result from an ingestion of a fumonisin or a fumonisin analog such as AAL toxins and include, for example, neoplastic conditions, toxicity, Neimann-Picks syndrome and Tay-Sachs disease.

EXPERIMENTAL PROCEDURES

All compounds listed in this application are commonly used and available and any abbreviation utilized is readily known to the skilled artisan.

Inhibition of Ceramide Synthase Activity in Rat Liver Microsomes and Reduced Conversion of [$^3$H] Sphingosine to [$^3$H] Ceramide by Intact Hepatocytes Materials—Fumonisin $B_1$ and $B_2$ were purchased from Division of Food Sciences and Technology, CSIR, Pretoria, South Africa. Tissue culture media were purchased from Gibco (Grand Island, N.Y.) and collagenase (Type IV), collagen (Type III), and palmitoyl-CoA were from Sigma (St. Louis, Mo.). Matrigel (from Engelbreth-Holm-Swarm (EHS) mouse tumor) were obtained from Collaborative Research Inc. (Bedford, Mass.) The [2-$^{14}$C] serine and the [$^3$H]sphingosine (prepared by catalytic exchange) were from New England Nuclear (Boston, Mass.). The sphingolipid standards were purchased from Sigma, or prepared synthetically (21).

Hepatocyte culture—Hepatocytes were prepared by a collagenase perfusion method, as known in the art as described in (22), from male Sprague-Dawley rats (125 to 200 g) fed a chow diet (Ralston Purina, St. Louis, Mo.) ad libitum. The hepatocytes were isolated using carefully aseptic procedures and plated in 60 mm tissue culture dishes coated with collagen for short term (<24 h) or with Matrigel for longer term (3 to 4 d) experiments. After plating for 4 h, the medium was changed to 2 ml of DMEM (with 3.7 g/L $NaHCO_3$) containing 10 μg/ml of insulin, 6.1 g/L of penicillin, 10 g/L of streptomycin sulfate, and varying concentrations of fumonisins (added from a 1 mM solution in Delbecco's phosphate buffered saline). The cells were maintained in a tissue culture incubator at 37° C. and an atmosphere of 5% $CO_2$; the medium was changed every 24 h. Cell viabilities were assessed by the ability of the cells to exclude 0.1% trypan blue, and were greater than 90%.

Lipid analyses—The de novo biosynthesis of sphingosine was measured, as known in the art as described in (23,24). Briefly, cells that had been exposed to fumonisins for 0 to 4 d were changed to new medium containing 10 μCi of [$^{14}$C]serine (25 mCi/mmol) in 2 ml of serine-free DMEM (Gibco) in the presence or absence of fumonisin. After incubation for 2 or 16 h, they were scraped from the dishes, 25 μg of carrier sphingosine and sphinganine were added, and the lipids were extracted and acid hydrolyzed to liberate the free long-chain bases using conditions that give optimal hydrolysis with minimal decomposition of the labile long-chain bases, as known in the art as described in (23–25). The sphinganine and sphingosine were separated by thin-layer chromatography on silica gel H (Brinkman) plates developed with $CHCl_3$:methanol:2N $NH_4OH$ (40:10:1, v/v/v) and the radiolabelling profile (shown in FIG. 2) was determined by radiometric scanning of the plates with a Bioscan System 200 Imaging Scanner. Sphingosine and sphinganine were visualized using ninhydrin, which also revealed any acid decomposition products, which migrate as a ninhydrin-positive material near the solvent front (when seen, the data were not considered reliable). The appropriate regions of the chromatoplate were scraped, placed in scintillation vials, and 0.2 ml of water and 4 ml of a detergent based scintillation cocktail were added. After several hours, the samples were counted with the appropriate corrections for quenching. In our experience (23,24,26,27), these procedures give a good representation of the total amount of label in the long-chain base moieties of cellular sphingolipids.

To measure the relative activity of ceramide synthase in intact hepatocytes, the cells were incubated with 1 $\mu$M fumonisin $B_1$ for 1 h, then 1 $\mu$Ci of [$^3$H]sphingosine was added and the cells were incubated for varying times. The [$^3$H]sphingosine was freshly purified because it decomposes rapidly to a material with an $R_f$ similar to that of ceramides on TLC. The [$^3$H]sphingosine was diluted to 1 Ci/mmol and applied to a small silica gel column (Unisil, Clarkston, Ill.) in chloroform. The column was washed with 10-column volumes of chloroform, the [$^3$H]sphingosine was eluted with methanol and the purity confirmed by TLC. The [$^3$H]sphingosine was transferred to a small test tube, the solvent was evaporated under $N_2$, a small volume of culture medium was added immediately, and the tube was sonicated for a few minutes using a bath-type sonicator. Aliquots of this solution were added to the cells, and at the end of the specified incubation period the cells were scraped from the dish, 25 $\mu$g of unlabelled ceramide carrier was added, and the lipids were extracted as described above. The [$^3$H]ceramides were separated from [$^3$H]sphingosine using silica gel H TLC plates developed with diethyl ether:methanol (99:1, v/v), visualized with $I_2$ vapor, and the amount of radiolabel was determined by scintillation counting Mass measurements of the long-chain bases were conducted by HPLC, as is known in the art as previously described in (28), with C20-sphinganine as an internal standard. To quantitate total sphingolipids, the extracts were acid hydrolyzed before preparing the samples for HPLC and corrected, if necessary, for any losses during hydrolysis or extraction by spiking replicate samples with a known amount of ceramide or sphingomyelin.

In vitro assays of serine palmitoyltransferase and ceramide synthase. A microsomal fraction was isolated from rat liver and assayed for serine palmitoyltransferase, as is known in the art as described in (24,29), and ceramide synthase, as is known in the art as described in (30), in the presence of varying concentrations of fumonisin $B_1$. The assay mixture for ceramide synthase contained 1 $\mu$M [$^3$H]sphingosine, 25 mM potassium phosphate buffer (pH 7.4), 0.5 mM dithiothreitol, 200 $\mu$M palmitoyl-CoA, and approximately 0.2 mg of microsomal protein in a total volume of 0.1 ml, which were found to be optimal assay conditions. The reaction was initiated by adding palmitoyl-CoA and, after incubation at 37° C. for 15 min, the products were extracted, resolved by TLC, and quantitated as described above. Background counts were subtracted using data from identical assays that omitted palmitoyl-CoA.

Other methods—The incorporation of radiolabel into other lipids was determined by separating the phospholipids by TLC using silica gel H plates developed with $CHCl_3$:methanol:formic acid:water (56:30:2:1, v/v/v/v), visualization of the spots and standards with $I_2$ vapor, and quantitation by scintillation counting. The amount of label in fatty acids was estimated using samples that had been incubated with 0.1M KOH in methanol for 1 h at 37° C. and separated using the ceramide TLC system because the methyl esters migrate near the solvent front under these conditions.

Results—Rat hepatocytes were selected as a model for the effects of fumonisins because *F. moniliforme* culture materials, now known to contain the cancer promoting fumonisin $B_1$ (9,15), are hepatotoxic and hepatocarcinogenic in the rat (4,10,31). Furthermore, sphingosine biosynthesis de novo by rat hepatocytes is relatively easy to follow using [$^{14}$C]serine, and proceeds via the reactions shown in FIG. 2 (24) like in other cells (23,32).

Figure 2:
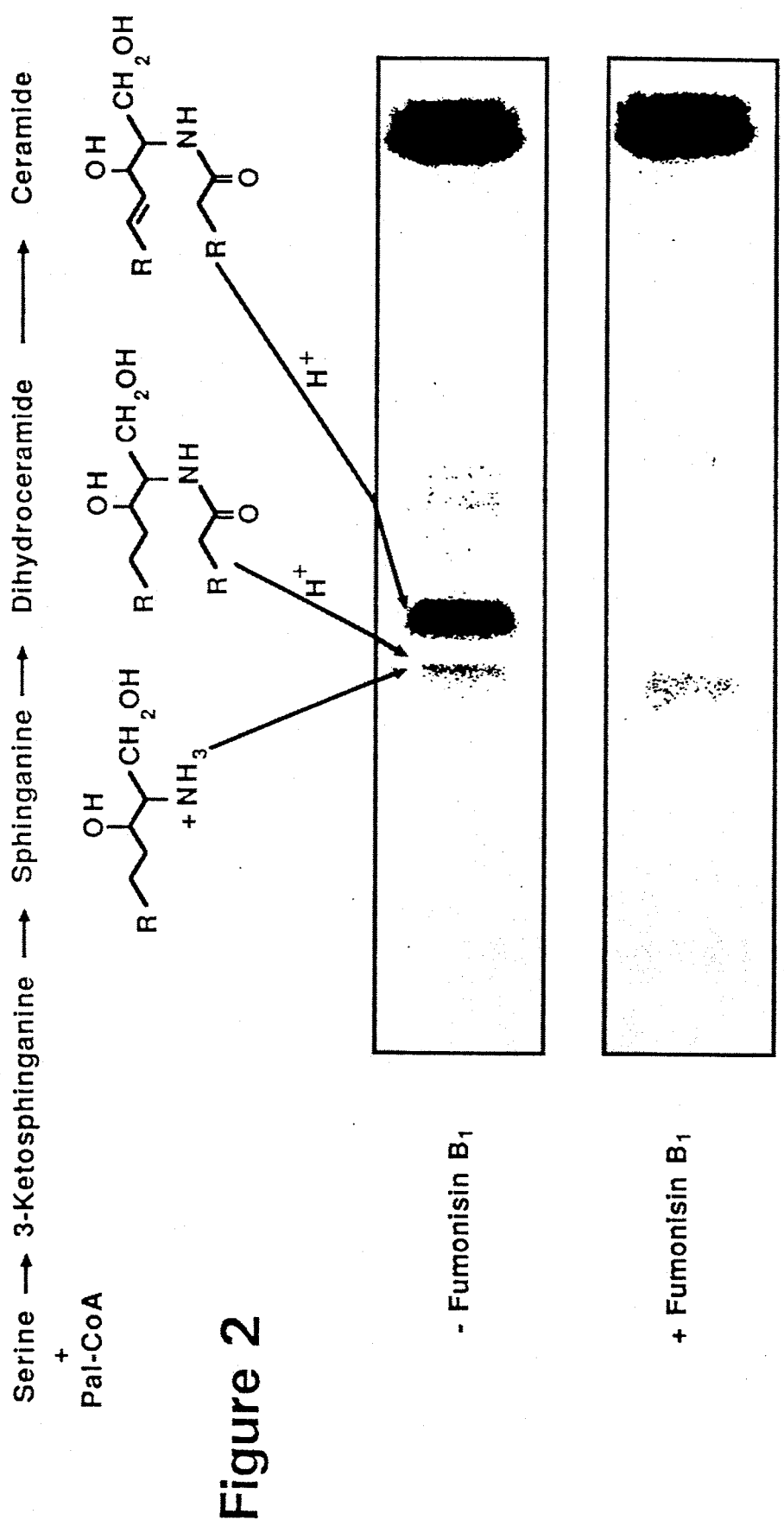
FIG. 2 shows sphingosine biosynthesis and inhibition by fumonisin $B_1$. Free long-chain bases (3-ketosphinganine, sphinganine, and sphingosine) have not been found to accumulate as detectable intermediates of this pathway under normal conditions; therefore, sphingosine formation is assessed by hydrolyzing the N-acyl products and analyzing the labelled long-chain bases as depicted in this figure. The chromatograms illustrate the labelling of sphinganine and sphingosine obtained by acid hydrolysis of the lipid extracts from hepatocytes incubated for 2 h with [$^{14}$C]serine with and without 1 $\mu$M fumonisin $B_1$. The large amount of radiolabel that migrates with the solvent front is primarily fatty acids.
Figure 3A:
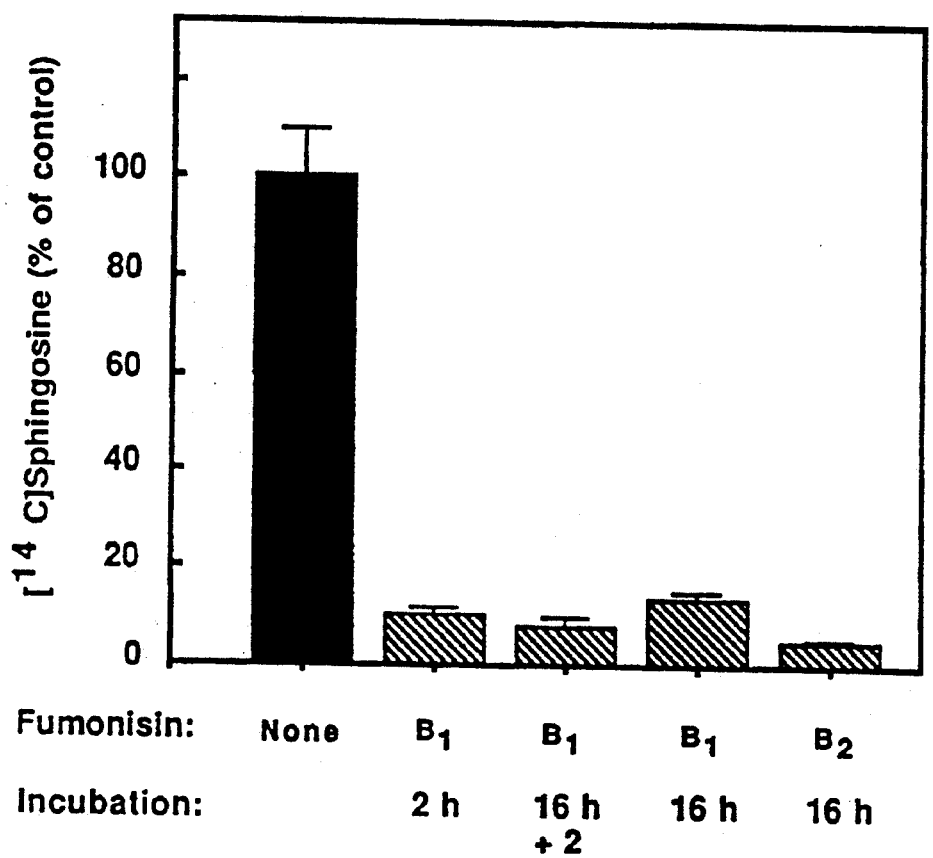
FIG. 3 shows time and concentration dependence of the inhibition of [$^{14}$C]serine incorporation into [$^{14}$C]sphingosine by fumonisins $B_1$ and $B_2$. Panel A: relative amounts of [$^{14}$C]sphingosine formed from [$^{14}$C]serine by hepatocytes exposed to no fumonisin $B_1$ (none), to 1 $\mu$M fumonisin $B_1$ and [$^{14}$C]serine for 2 h (2 h), upon pretreatment with 1 $\mu$M fumonisin $B_1$ for 16 h followed by incubation with [$^{14}$C]serine for 2 h, and to 1 μM fumonisin $B_1$ or $B_2$ and [$^{14}$C]serine for 16 h. Panel B: concentration dependence of fumonisin $B_1$ inhibition of [$^{14}$C]serine incorporation into [$^{14}$C]sphingosine by rat liver hepatocytes. The assay conditions for this experiment were the same as for the 2 h incubations described in FIG. 2, and each data point represents the mean ±SD for triplicate dishes of hepatocytes. All of the groups were significantly different from the untreated control ($P<0.05$).
Figure 3B:
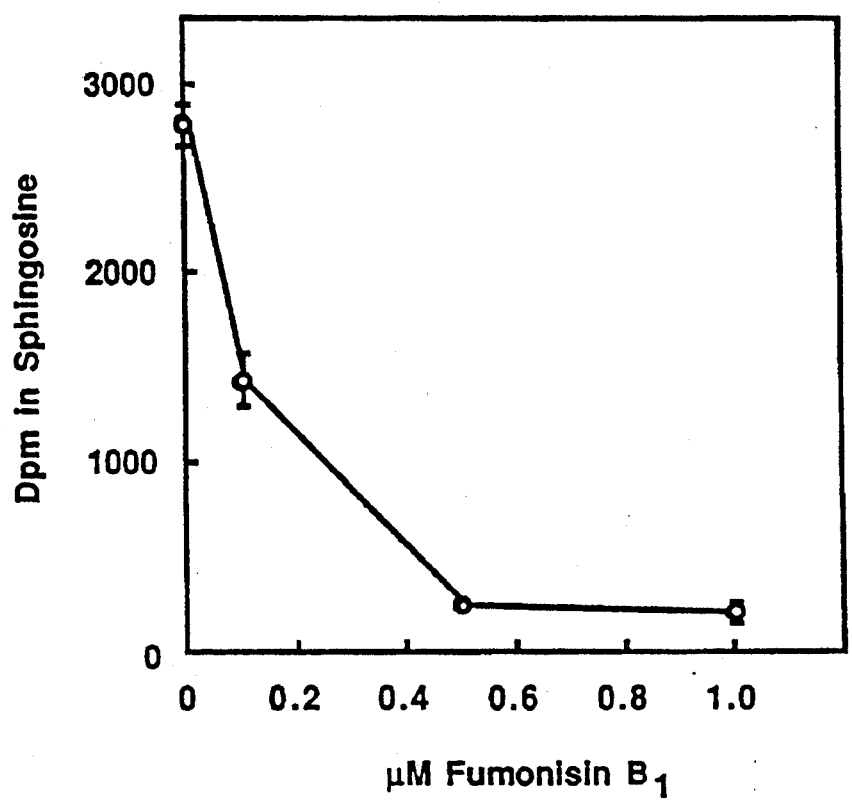

Fumonisin $B_1$ (1 $\mu$M) caused an almost complete inhibition of [$^{14}$C]sphingosine formation by hepatocytes (FIGS. 2 and 3). Similar inhibition occurred when [$^{14}$C]serine and fumonisin $B_1$ were added together for short term (2 h) or overnight (16 h) incubations and when the cells were incubated overnight with fumonisin before adding [$^{14}$C]serine (FIG. 3A, the 16 h+2h group). Hence, fumonisin $B_1$ appears to act fairly quickly, and the inhibition is persistent. The $IC_{50}$ for inhibition of [$^{14}$C]serine incorporation into [$^{14}$C]sphingosine was approximately 0.1 $\mu$M for fumonisin $B_1$ (FIG. 3B). A similar degree of inhibition was obtained with fumonisin $B_2$ (FIG. 3A), another mycotoxin often produced in substantial amounts by *F. moniliforme* (10).

In contrast, there was no reduction in the radiolabelling of phosphatidylserine, phosphatidylethanolamine, or phosphatidylcholine from [$^{14}$C]serine (Table 1), nor in the mass of these phospholipids under conditions where sphingolipid labelling (FIGS. 2 and 3) and mass (Table 1) were reduced significantly. Fatty acid biosynthesis from [$^{14}$C]acetic acid was not altered (Table 1).

| Effects of Fumonisin $B_1$ on selected lipids of rat hepatocytes[a] | | | |
|---|---|---|---|
| | \multicolumn{3}{c}{$\mu$M Fumonisin $B_1$} | | |
| Parameter[a] | 0 | 1 | 10 |
| A. Radiolabelling | (Dpm/mg protein $\times 10^{-3}$) Mean $\pm$ SD | | |
| Phosphatidylethanolamine | 103 $\pm$ 8.3 | 163 $\pm$ 4.4* | 153 $\pm$ 10* |
| Phosphatidylserine | 44.9 $\pm$ 9.5 | 48.8 $\pm$ 2.9 | 52.3 $\pm$ 3.6 |
| Phosphatidylcholine | 2270 $\pm$ 226 | 2640 $\pm$ 264 | 2740 $\pm$ 196* |
| Base labile fatty acids[b] | 2055 $\pm$ 261 | 2075 $\pm$ 54 | 2075 $\pm$ 103 |
| B. Mass measurements[c] | (nmol/mg protein) Mean $\pm$ SD | | |
| Phosphatidylethanolamine | 44.1 $\pm$ 2.9 | 44.9 $\pm$ 1.4 | 44.4 $\pm$ 0.9 |
| Phosphatidylserine | 13.8 $\pm$ 2.8 | 15.5 $\pm$ 2.6 | 12.3 $\pm$ 1.9 |
| Phosphatidylcholine | 118 $\pm$ 3.6 | 105 $\pm$ 1.8 | 112 $\pm$ 3.4 |
| Total sphingolipids | 8.9 $\pm$ 0.9 | 6.7 $\pm$ 0.3* | 6.5 $\pm$ 0.7* |

[a]Hepatocytes were incubated for 16 h with [$^{14}$C]serine and the concentrations of fumonisin $B_1$ shown using the conditions described in FIG. 2. The lipids were extracted, separated by thin-layer chromatography, and quantitated as described in the text.
*The groups that are significantly different (P < 0.05) from the control (no fumonisin) group are designated by asterisks.
[b]Determined after incubation with 10 $\mu$Ci of [$^{14}$C]acetic acid.
[c]Determined by phosphate analyses (27) with the exception of the total sphingolipids, which were estimated by acid hydrolysis of the lipid extracts and analysis of the amount of sphingosine by HPLC (28).

Hence, the inhibition of sphingolipid biosynthesis does not appear to be due to the inability of the cells to take up [$^{14}$C]serine and to incorporate it into lipids in general, nor to affect the ability of the cell to form the other biosynthetic precursors (i.e., fatty acids).

Although de novo sphingolipid biosynthesis was completely blocked by 10 $\mu$M fumonisin $B_1$, there was only a slight reduction in the mass of total sphingolipids after 1 d (Table 1). This is probably due to the generally slow turnover of sphingolipids (32). A greater effect was seen when the cells were plated on Matrigel to allow incubation with 1 $\mu$M fumonisin $B_1$ for 4 d, which reduced the level of total sphingolipids by about half (i.e., from 4.6$\pm$0.7 nmol/dish to 2.1$\pm$0.1 nmol/dish).

There was no decrease in the number of viable cells despite treatment with 1 μM fumonisin for 4 d.

There are several potential sites at which fumonisins might affect sphingosine metabolism (FIG. 2); hence, these were investigated further. Fumonisins do not appear to act at the first step of this pathway because even a fairly high concentration (25 μM) fumonisin $B_1$ did not reduce the activity of serine palmitoyltransferase in vitro (i.e., the activities in the presence and absence of 25 μM fumonisin $B_1$ were 88±3 and 61±15 pmol 3-ketosphinganine formed/min/mg of microsomal protein, respectively). Furthermore, treatment of hepatocytes with fumonisin $B_1$ followed by assays of this enzyme in disrupted cells revealed no inhibition (i.e., the activities were 7.7±0.2 and 8.2±0.8 pmol/min per mg of cellular protein in the presence and absence of 2.5 μM fumonisin $B_1$, respectively). Inhibition at the second step of the pathway is also unlikely because 3-ketosphinganine was not seen to accumulate (FIG. 2), and there was no reduction in the formation of [$^{14}$C]sphinganine.

Figure 4A:
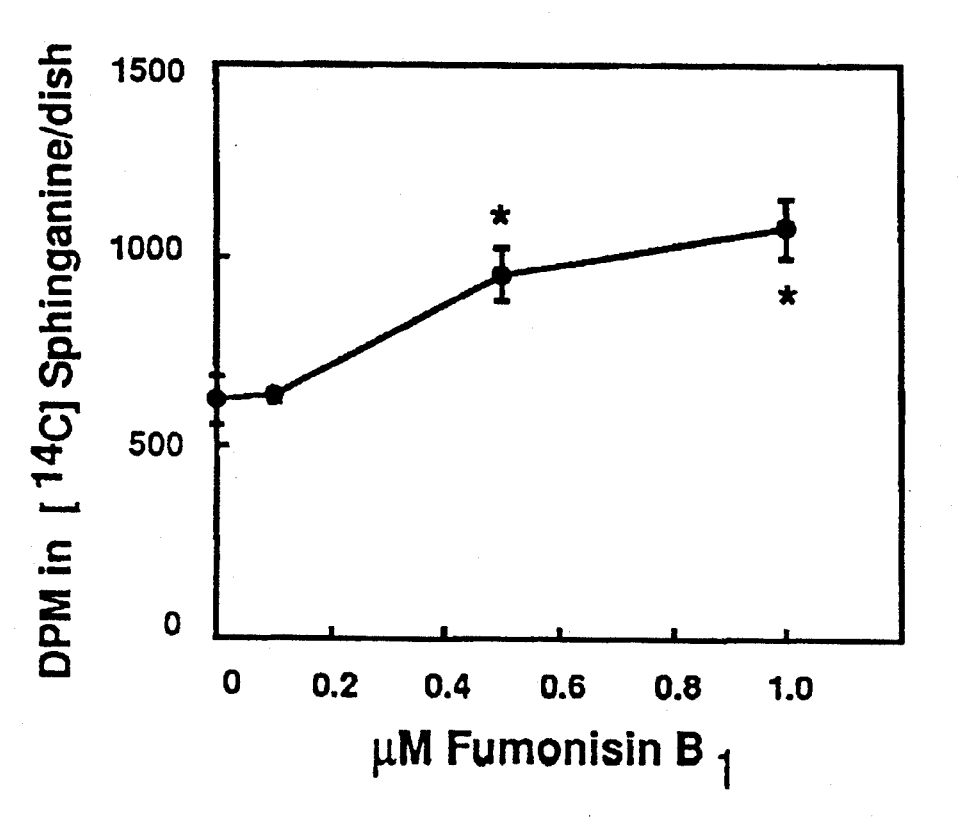
Figure 4B:
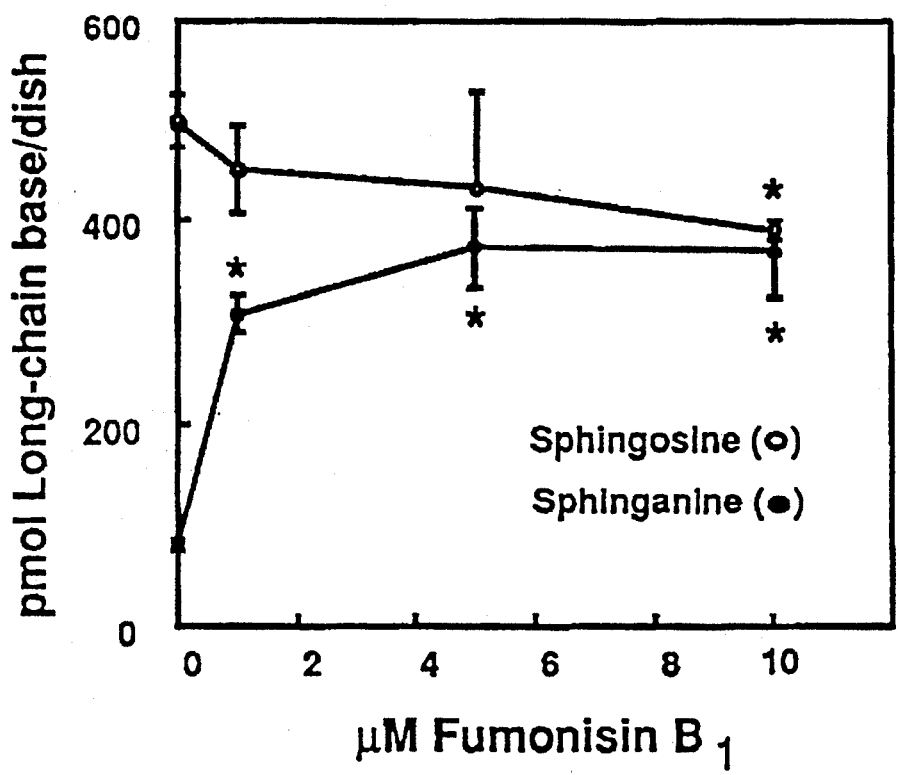
FIG. 4 shows increases in sphinganine upon incubating hepatocytes with fumonisin $B_1$. A: Amounts of label detected in [$^{14}$C]sphinganine; the conditions for these analyses were the same as in FIGS. 2 and 3; B: Mass amounts of sphingosine and sphinganine after incubation of hepatocytes with fumonisin $B_1$ for 2 h, with analysis of the free long-chain bases by HPLC (28); C: HPLC profile of the free long-chain bases of rat liver hepatocytes after incubation with 1 μM fumonisin $B_1$ for 2 h (for comparison with the usual HPLC profile of untreated liver see reference 28); D: Inhibition of [$^3$H]sphingosine conversion to ceramides by fumonisin $B_1$. Hepatocytes were incubated with 1 μM fumonisin $B_1$ for 1 h, then approximately 1 μCi of [$^3$H]sphingosine was added and the cells were incubated for the times shown. The lipids were extracted and analyzed by TLC as described in the text. Asterisks designate the groups that are different from control (no fumonisin treatment) with $P<0.05$.
Figure 4C:
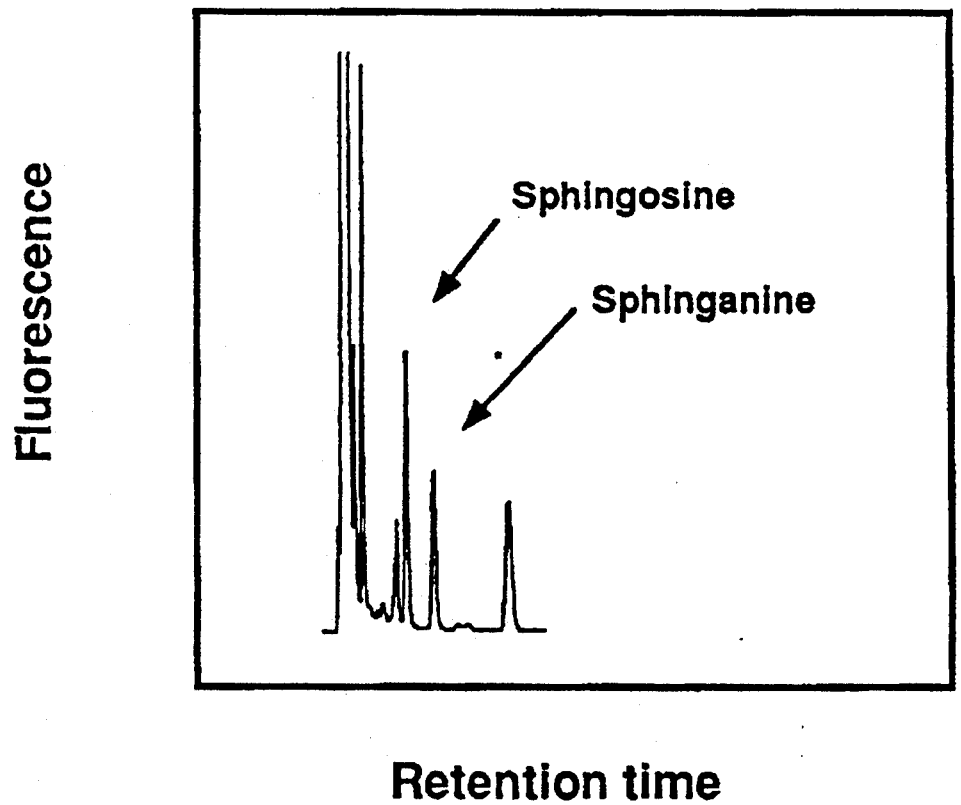

Fumonisins do inhibit at the step where [$^{14}$C]sphinganine is converted to N-acyl[$^{14}$C]sphinganine because the amount of radiolabel in [$^{14}$C]sphinganine increased when hepatocytes were treated with fumonisin $B_1$ (FIG. 4A). This was accompanied by an increase in the mass of free sphinganine (FIGS. 4B and C); when hepatocytes were incubated with 1 μM fumonisin $B_1$ for 4 d, sphinganine increased 110 fold (i.e., to 1499±18 pmol/dish compared to 13.6±0.4 pmol/dish for the control). There was only a small reduction in the amount of free sphingosine within the first 2 h (FIG. 4B); however, free sphingosine decreased significantly after 4 d (i.e., to 52±1 pmol/dish compared to 233±14 pmol/dish for the control). These findings are consistent with the view that the free sphingosine found in hepatocytes is not an intermediate of the de novo biosynthetic pathway (23,24) (hence, will be affected little by short term treatment with fumonisin $B_1$) but arises from the turnover of complex sphingolipids (27,32) and would, therefore, be most affected when there is a decrease in total sphingolipids due to longer term exposure to these compounds.

Figure 4D:
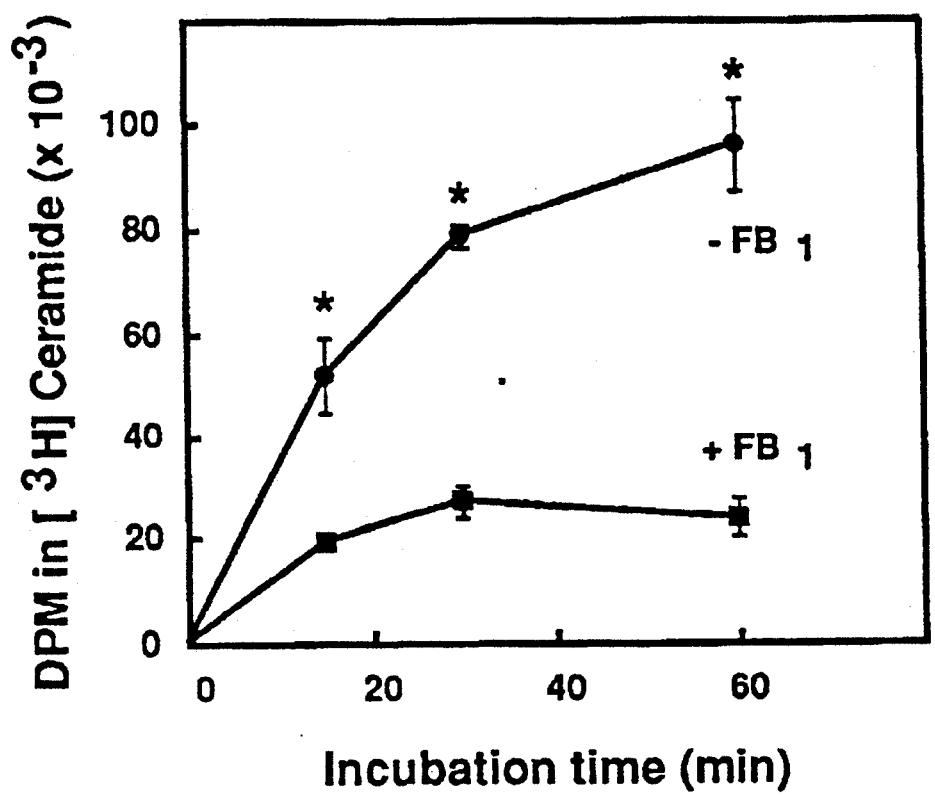
Figure 5:
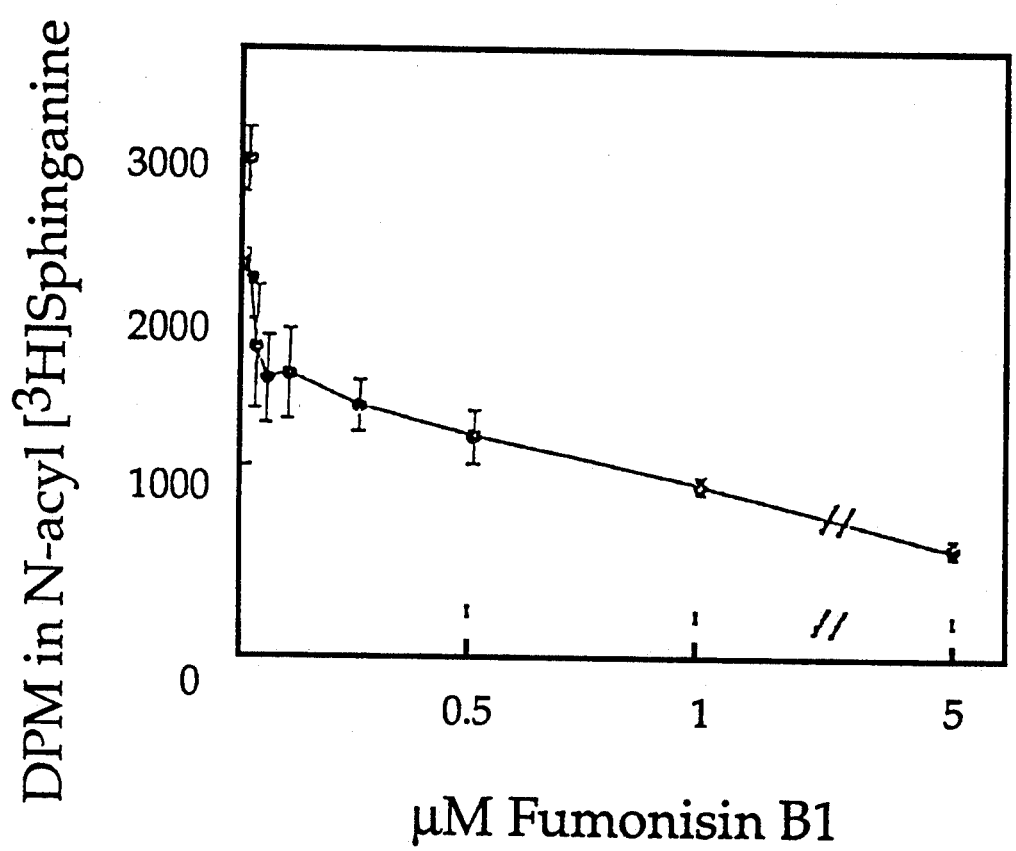
FIG. 5 shows inhibition of ceramide synthase by fumonisin $B_1$ in vitro.

Inhibition at this step of the pathway was demonstrated directly by in vitro assays of ceramide synthase, which has been reported to acylate both sphinganine and sphingosine (30) (FIG. 5) and by following the conversion of [$^{3}$H]sphingosine to [$^{3}$H]ceramide by intact cells (FIG. 4D). The apparent IC$_{50}$ for inhibition of this activity in vitro was approximately 0.1 μM for fumonisin $B_1$, but the inhibition may be biphasic (FIG. 5). All together, these findings demonstrate that the inhibition of ceramide synthase accounts for the disruption of de novo sphingolipid biosynthesis by fumonisins, although these compounds may have additional effects on other enzymes of sphingolipid metabolism.

Figure 6:
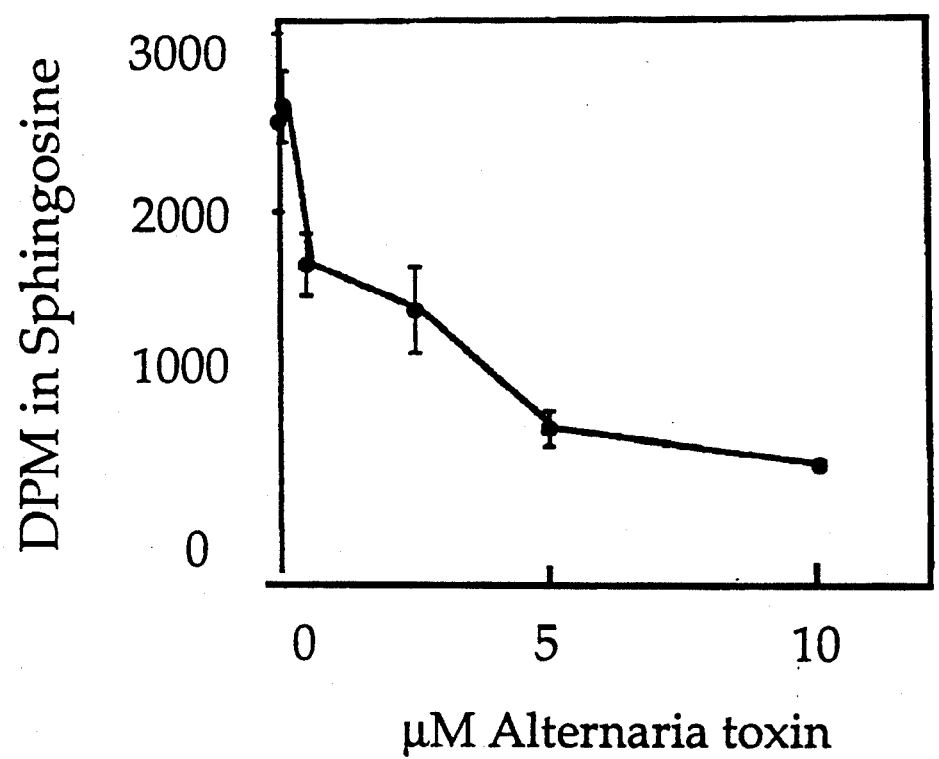
FIG. 6 shows inhibition of de novo sphingosine production upon incubation of rat hepatocytes with Alternaria toxins (AAL toxins).
Figure 7A:
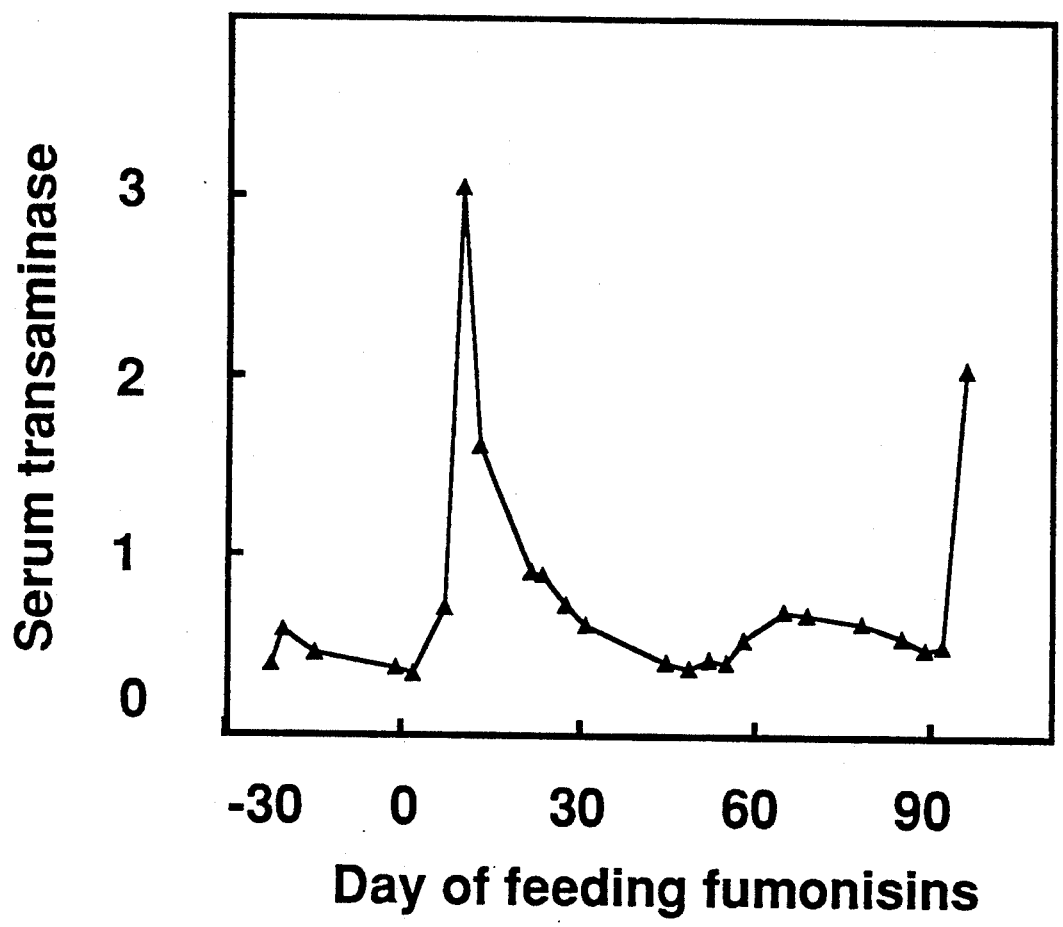
FIG. 7 shows the concentration of sphingosine, sphinganine and their ratio over time in the plasma of a pony fed fumonisin-contaminated food.
Figure 7B:
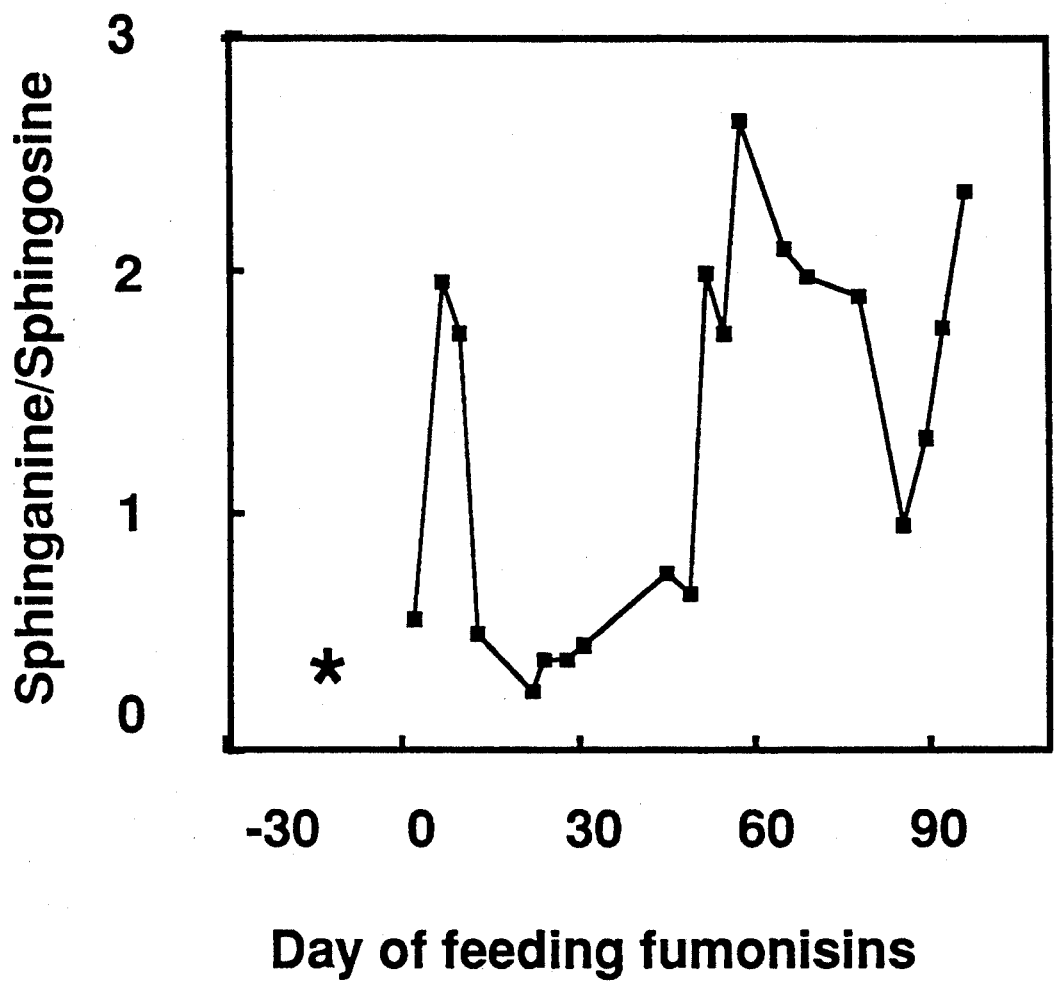
Figure 7C:
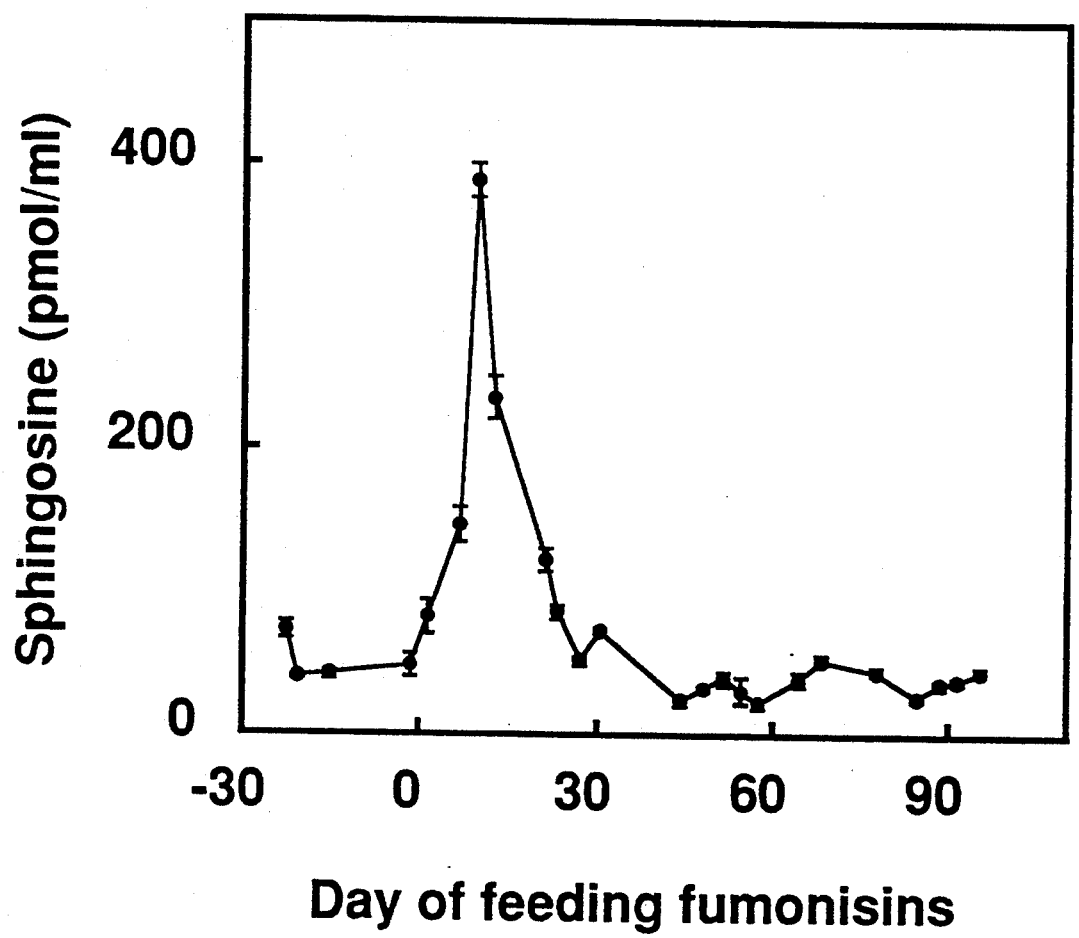
Figure 7D:
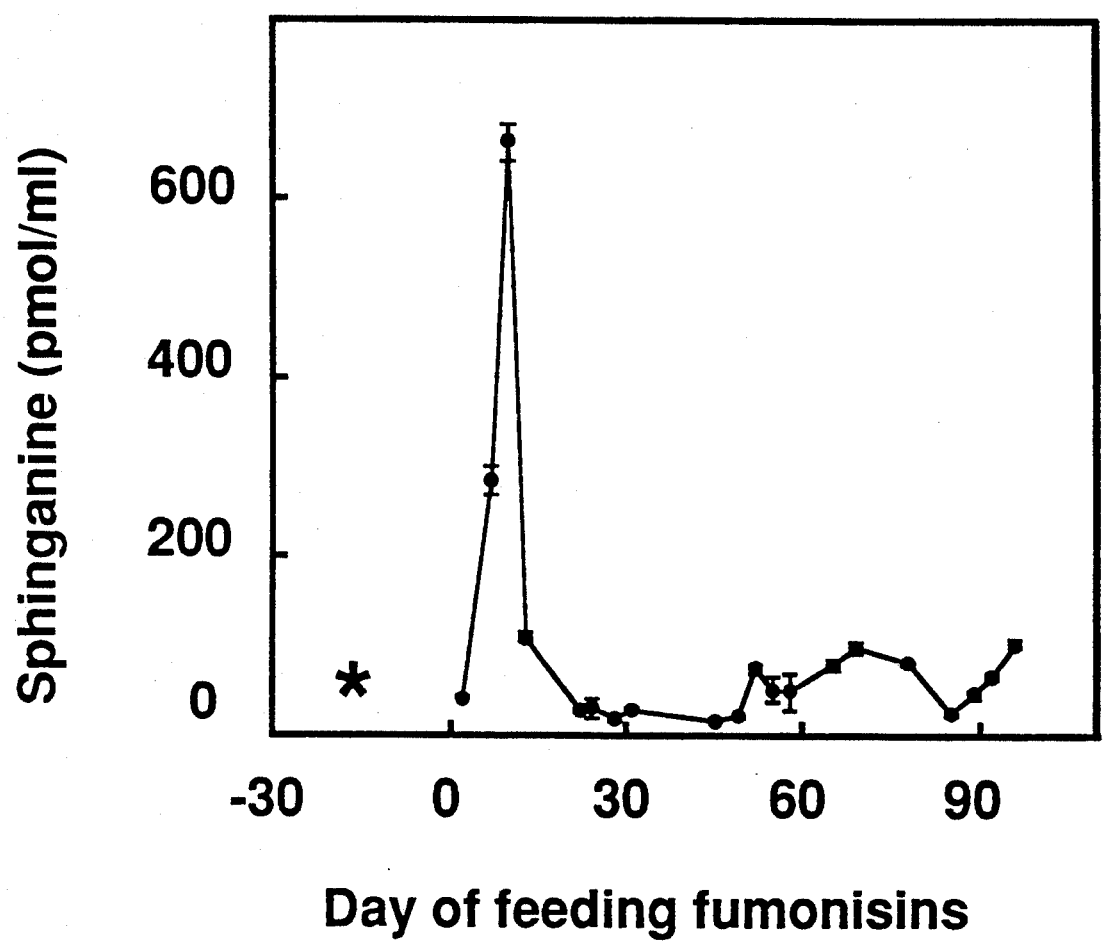

The structural basis for this inhibition is due to similarities between the fumonisins and long-chain (sphingoid) bases (FIG. 1), which likely allow them to be recognized as substrate (or transition state or product) analogs by ceramide synthase. The absence of a hydroxyl group at carbon 1 may alter their orientation in the active site of this enzyme and preclude acylation or, if acylated, result in an inhibitory ceramide that cannot be removed by addition of a sphingolipid head group at that position. As shown in FIG. 1, the lack of a hydroxymethyl group at position 1 is shared by a number of other fumonisin-like compounds, such as the host-specific phytotoxins produced by another fungus, *Alternaria alternata* f. sp. *lycopersici* (33); hence, more naturally occurring inhibitors of this pathway exist. Data on the Alternaria toxins (AAL toxins) shown in FIG. 1 demonstrates inhibition similar to that of fumonisins (FIG. 6). Specifically, when Alternaria toxins were added to hepatocytes, there was a dose-dependent reduction in the formation of sphingolipids. In other experiments (not shown) we have also found that Alternaria toxins (AAL toxins) inhibit ceramide synthase in vitro. These compounds are also unable to follow the usual pathway of long-chain base catabolism, which proceeds via phosphorylation at position 1 (32), and this may contribute to the persistence of the inhibition.

These findings with rat hepatocytes provide the first identification of a biochemical target for the action of fumonisins, and demonstrate that inhibition of de novo sphingolipid biosynthesis in vitro may underlie the hepatotoxicity and hepatocarcinogenicity of this mycotoxin in vivo. The hepatic levels of fumonisins under these conditions are not known; however, if all the fumonisin given in feeding studies with rats (1 to 10 mg) (3-5,31) was distributed uniformly in the body, the concentrations could be between 10 and 100 μM. This is surely an over- (or under-) estimation of the amount that reaches liver in vivo, but certainly considerably higher than the IC$_{50}$ for inhibition of sphingolipid biosynthesis by hepatocytes (0.1 μM). In other studies, we have noted a 10 and 35% reduction in [$^{14}$C]sphingosine biosynthesis by hepatocytes isolated from two rats given fumonisin $B_1$ (5 mg/200 g body weight) by gavage for just 2 days. There was also a pronounced reduction in the ratio of free [$^{14}$C]sphingosine to [$^{14}$C]sphinganine from 2.6±0.14 (a typical ratio for control hepatocytes) to 0.5±0.1.

Disruption of this pathway is an attractive mechanism for the pathological effects of fumonisins since sphingolipids are involved in regulating various aspects of cell growth, differentiation, and transformation (18-20). For example, the degeneration of neuronal cells seen in equine leucoencephalomalacia can be due to inhibition of sphingolipid biosynthesis because brain contains high levels of sphingolipids (17). Also, an accumulation of sphinganine in cells exposed to fumonisins can lead to cell death since long-chain bases can be highly cytotoxic (34,35), or to cell proliferation since these compounds are mitogenic to some cell types (36) and affect diverse cell systems (20), including protein kinase C (37), the epidermal growth factor receptor (38), the $Na^+/K^+$ ATPase (39) and phosphatidic acid phosphohydrolase (40), inter alia. Thus, although toxic, fumonisins (or related compounds) can be therapeutically useful in diseases where defects in sphingolipid turnover cause cells to accumulate high levels of sphingolipids.

Alteration of Serum Sphingolipids upon Dietary Exposure of Ponies to Fumonisins, Mycotoxins Produced by *Fusarium moniliforme*

Materials—Corn screenings were ground in a Romer Mill (Romer Labs, Chesterfield, Mo.) and mixed thoroughly. Samples were taken from each lot and analyzed for fumonisins by high-performance liquid chromatography (HPLC) and thin-layer chromatography as is known in the art as previously described in (15). If the amounts of fumonisin B1 showed greater than 10% variation (relative standard deviation in 8 samples from each 25 kg lot), the lot was mixed, sampled, and analyzed a second time or until variance was less than 10%. Using the mean fumonisin B level, individual rations were prepared daily by adding the corn screenings to pellets (NADC Horse Ration, Code 560, Purina Mills, St. Louis, Mo.) and molasses (Promolas Easy Mixer Supreme, Pacific Molasses Co., San Francisco, Calif.) to yield the fumonisin concentrations cited in the text. In general, the ration contained 60% pellets, 10% molasses, and 30% corn screenings. The control diet consisted of pellets plus molasses.

All portions of the diet were subjected to general screens for toxicants by gas chromatography/mass spectroscopy and inductively coupled plasma spectroscopy, and assayed for chlorinated hydrocarbon pesticides, organophosphate pesticides, carbamate pesticides, aflatoxins, zearalenol, T-2 toxin, diacetoxyscirpenol, deoxynivalenol, 15-acetyl deoxynivalenol, fusarenone-x, zearalenenone, HT-2 toxin, T-2 tetrol, sterigmatocystin, cyclopiazonic acid, ochratoxin A, gliotoxin, sporodesmin, and griseofulvin. In addition, the hay, molasses, and pellets were tested for fumonisin B1 and B2.

Feeding protocols—Clinically normal ponies of varying age and sex were conditioned on the control diet for 21 days prior to the trial. Horse 341 was a 6 year old gelding (173-193 Kg), 299 was a 12 year old mare (205-215 Kg), 164 was a 12 year old mare (206-290 Kg) and 166 was a 16 year old mare (143-164 Kg). During the conditioning period and throughout the trial, all ponies received alfalfa hay by free choice. The test groups were fed varying levels of fumonisin (15 to 44 ppm) for varying lengths of time. The individual unconsumed rations were measured daily; at certain times, the ponies consumed variable portions of the rations, and these have been indicated in the figures.

Analysis of serum long-chain bases—Blood was drawn approximately twice a week, centrifuged to obtain serum, and aliquots were frozen for analyses of free sphingosine and sphinganine by HPLC as is known in the art as described in (28). To quantitate total sphingolipids in some samples, the extracts were acid hydrolyzed before preparing the samples for HPLC.

Clinical chemistry, evaluation, and tissue collection—The following clinical chemistry parameters were also analyzed with blood: total bilirubin, direct bilirubin, urea nitrogen, alkaline phosphatase, AST/SGOT, creatine kinase, gamma glutamyl transaminase, and bile acids. The animals were observed intermittently throughout each day and behavior changes were noted. Animals that were euthanized or died underwent a routine necropsy, and brain, liver, and kidney were prepared for microscopic study.

Results—Analyses of sera from three ponies that had not been exposed to fumonisin contaminated feed produced HPLC profiles like the one shown in Table 2.

TABLE 2

| PEAK NO. | TIME | AREA | CONC |
|---|---|---|---|
| 1 | 1.088 | 20366 | 0.0898 |
| 2 | 1.733 | 22118978 | 97.5714 |
| 3 | 2.413 | 134152 | 0.5918 |
| 4 | 2.944 | 94677 | 0.4176 |
| 5 | 3.971 | 4455 | 0.0197 |
| 6 | 4.2 | 2677 | 0.0118 |
| 7 | 4.47 | 773 | 0.0034 |
| 8 | 5.21 | 2416 | 0.0107 |
| 9 | 5.483 | 2141 | 0.0094 |
| 10 | 6.283 | 11185 | 0.0493 |
| 11 | 8.28 | 3517 | 0.0155 |
| 12 | 13.688 | 274192 | 1.2095 |
| TOTAL | | 22669520 | 100 |

Sphingosine elutes at 6.3 min and, for this sample, sphinganine (at 8.3 min) can also be seen clearly. In some instances, the amount of sphinganine was too low to detect above background. The compound eluting at 13.7 min is the internal standard (C20-sphinganine) that is added to aid extraction and quantitation of the long-chain bases (28).

Data for sera collected from three ponies at intervals of 2 weeks to 9 months are given in Table 3.

TABLE 3

Levels of free long-chain bases in sera from four ponies given feed thought to be free of contamination by fumonisins.

| Days after initial sampling | Sphingosine pmol/ml | Sphinganine pmol/ml | Ratio Sa/So |
|---|---|---|---|
| Pony #299 | | | |
| 0 | 46.8 ± 1.2 | 13.6 ± 0.4 | 0.29 |
| 14 | 39.3 ± 1.6 | 10.9 ± 1.2 | 0.28 |
| 65 | 107 ± 18 | 22.9 ± 6.0 | 0.19 |
| 248 | 59.3 ± 6.0 | 16.4 ± 6.4 | 0.26 |
| Pony #164 | | | |
| 0 | 118 ± 5 | 22.6 ± 4.6 | 0.19 |
| 2 | 97 ± 10 | 32.4 ± 8.0 | 0.32 |
| 7 | 63 ± 1 | 27.3 ± 1.4 | 0.43 |
| 22 | 42 ± 2 | 11.7 ± 4.0 | 0.26 |
| Pony #166 | | | |
| 0 | 82 ± 24 | 22.2 ± 1.8 | 0.25 |
| 2 | 33 ± 1 | 20.7 ± 0.2 | 0.63 |
| 7 | 54 ± 1 | 20.8 ± 2.0 | 0.40 |
| 22 | 43 ± 4 | 13.7 ± 0.6 | 0.32 |

Sphingosine is the predominant free long-chain base in serum from all ponies. The mean ±SD for all of the analyses (n=12) were: 65±29 pmol sphingosine/ml serum and 19.5±6.5 pmol sphinganine/ml serum. There were some variability in the amounts of these compounds over time, although this was seen less in sphinganine than sphingosine; furthermore, the sphinganine to sphingosine ratio (0.32±0.12) was fairly constant. This latter parameter may be useful because these compounds are sometimes difficult to extract efficiently; hence, a ratio of two structurally related species (i.e., sphinganine and sphingosine versus the C20-sphinganine standard or sphinganine versus sphingosine) will be more accurate than absolute measurements of the mass of a single compound.

Table 4 illustrates a serum sample from the same pony as in Table 2 after exposure to fumonisin-contaminated feed.

TABLE 4

| PEAK NO. | TIME | AREA | CONC |
|---|---|---|---|
| 1 | 1.091 | 23970 | 0.1095 |
| 2 | 1.733 | 21355228 | 97.5859 |
| 3 | 2.412 | 74417 | 0.3401 |
| 4 | 2.945 | 97222 | 0.4443 |
| 5 | 4.166 | 17641 | 0.0806 |
| 6 | 5.09 | 11076 | 0.0506 |
| 7 | 5.507 | 2952 | 0.0135 |
| 8 | 5.883 | 2220 | 0.0101 |
| 9 | 6.328 | 47332 | 0.2163 |
| 10 | 7.627 | 1052 | 0.0048 |
| 11 | 8.326 | 70389 | 0.3217 |
| 12 | 13.761 | 180023 | 0.8226 |
| TOTAL | | 21883512 | 100 |

Difference in the HPLC profile are evident both on the magnitude of the peaks and the relative amounts of sphingosine and sphinganine. The levels of sphingosine and sphinganine are summarized in Table 5 for two ponies given 44 ppm fumonisin B1, a level that is often toxic and resulted in ELEM in both of these animals (pony 164 died after 10 days and pony 166 was euthanized on day 45).

TABLE 5

Levels of free long-chain bases in sera from two ponies given feed contaminated with fumonisin B1 at 44 ppm

| Day of Trial | Sphingosine pmol/ml | Sphinganine pmol/ml | Ratio Sa/So | AST/SGOT Units |
|---|---|---|---|---|
| Pony #164[1] | | | | |
| −1 | 42 ± 2 | 11.7 ± 4.0 | 0.26 | 248 |
| 2 | 117 ± 7 | 70.2 ± 4.2 | 0.60 | 235 |
| 7 | 152 ± 13 | 253 ± 22 | 1.67 | 357 |
| 10 | 226 ± 20 | 283 ± 18 | 1.25 | 4000 |
| Pony #166[2] | | | | |
| −1 | 43 ± 4 | 13.7 ± 0.6 | 0.32 | 210 |
| 2 | 43 ± 6 | 37.2 ± 0.2 | 0.87 | 199 |
| 7 | 66 ± 16 | 62 ± 8 | 0.95 | 215 |
| 10 | 92 ± 4 | 179 ± 8 | 1.92 | 1470 |
| 13 | 100 ± 8 | 174 ± 18 | 1.72 | 2080 |

[1]Pony was described as nervous and off feed from day 5; by day 9 was blind and down, and on day 10 had full clinical signs of ELEM and died that evening.
[2]Pony was described as lethargic from day 5; off feed from day 8; later put back on full feed and exhibited CNS signs; was euthanized on day 45.

By day 2, pony 164 exhibited elevations in sphingosine and sphinganine; however, the increase in sphinganine was greatest (6-fold compared to the level immediately prior to feeding fumonisin) and this was reflected in an increase in the ratio of sphinganine to sphingosine, which doubled. By day 7, sphinganine had increased 22-fold and sphingosine was 3.6-fold compared to the initial level. The pronounced increase in sphinganine over sphingosine gave a sphinganine to sphingosine ratio (1.67) that is unprecedented in any previous analyses of long-chain bases in mammalian systems—except our above studies of the effects of fumonisins on hepatocytes.

Pony 166 also showed an increase in sphinganine (2.7 fold), but not sphingosine, after only two days on contaminated feed, the earliest timepoint examined. By day 7, sphingosine and sphinganine were both elevated, but sphinganine had increased to the level of sphingosine. By day 10, pony 166 showed elevations in sphingosine (2-fold), sphinganine (13-fold), and AST/SGOT (7-fold) that indicate significant hepatic injury.

Another pony (#212) was initially given 44 ppm of fumonisin, but less was eaten because of variable consumption of the feed and because the fumonisin was withheld for two weeks. The results for this animal are shown in FIG. 7. As for the other two ponies, there was a rapid increase in free long-chain bases that slightly preceded the clinical signs of toxicity (i.e., elevated AST/SGOT). Within 2 days the sphingosine level had nearly doubled over the amount the day prior to administration of contaminated feed (i.e., from 49.1±5 pmol to 147±5 pmol); sphinganine was also elevated but the fold increase could not be calculated because sphinganine was not detectable in serum from this pony before the trial. By 7 days, sphingosine had increased another 2-fold, but sphinganine was 6.7 fold higher than the level at day 2, and now exceeded the level of sphingosine by 1.9 fold. After day 10 of the study, both sphinganine and sphingosine decreased, although the ratio remained elevated above that before exposure to fumonisin. The decrease was during the period where the pony consumed variable amounts of the contaminated feed (i.e., from day 5 through 31) and when the feed was withdrawn all together. The contaminated feed was provided again on day 45 and was consumed variably until termination of the study on day 97. Restoration of the fumonisin resulted in small increases in sphingosine and sphinganine, but most prominently in the sphinganine to sphingosine ratio of 2 to 3. This behavior suggests that serum sphingosine and sphinganine, and most especially their ratio, increases after fumonisin exposure, returns to more normal levels upon removal of (or more variable consumption of) contaminated feed, and increases again when the animals are reexposed to fumonisin in the diet.

Figure 8A:
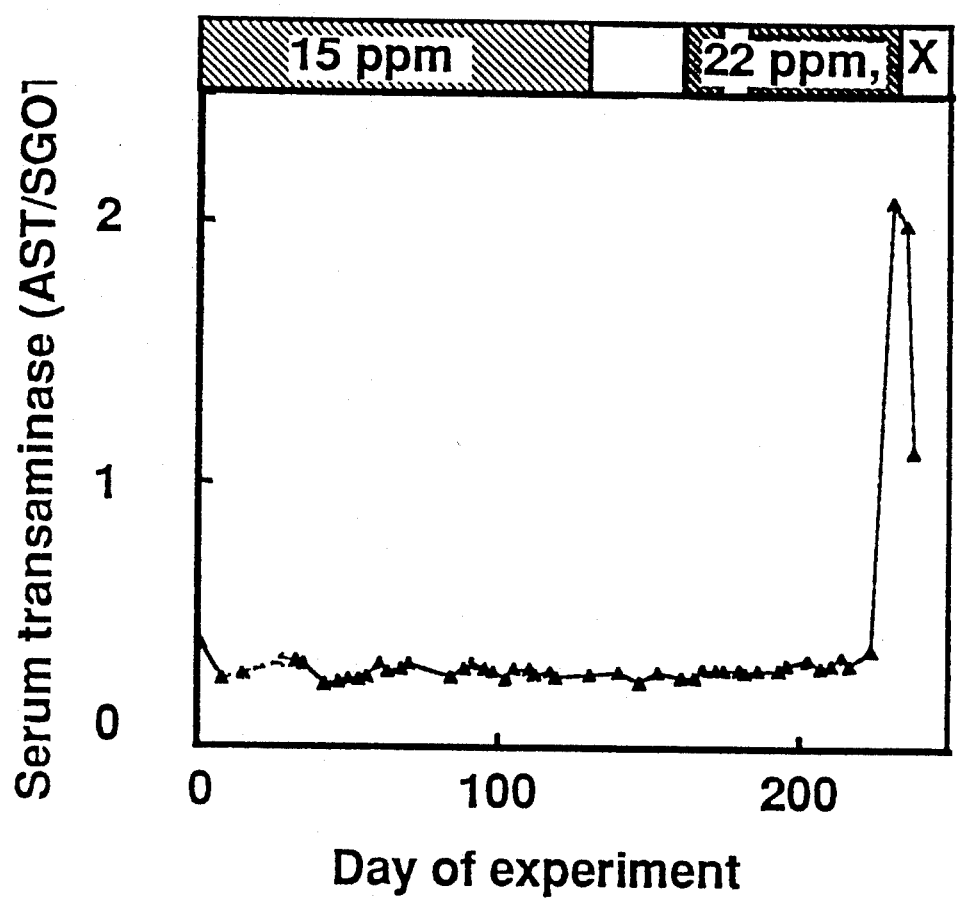
FIG. 8 shows the plots of AST/SGOT and sphinganine to sphingosine ratio over time in the plasma of a pony fed fumonisin-contaminated feed at 15 and 22 ppm fumonisin $B_1$.
Figure 8B:
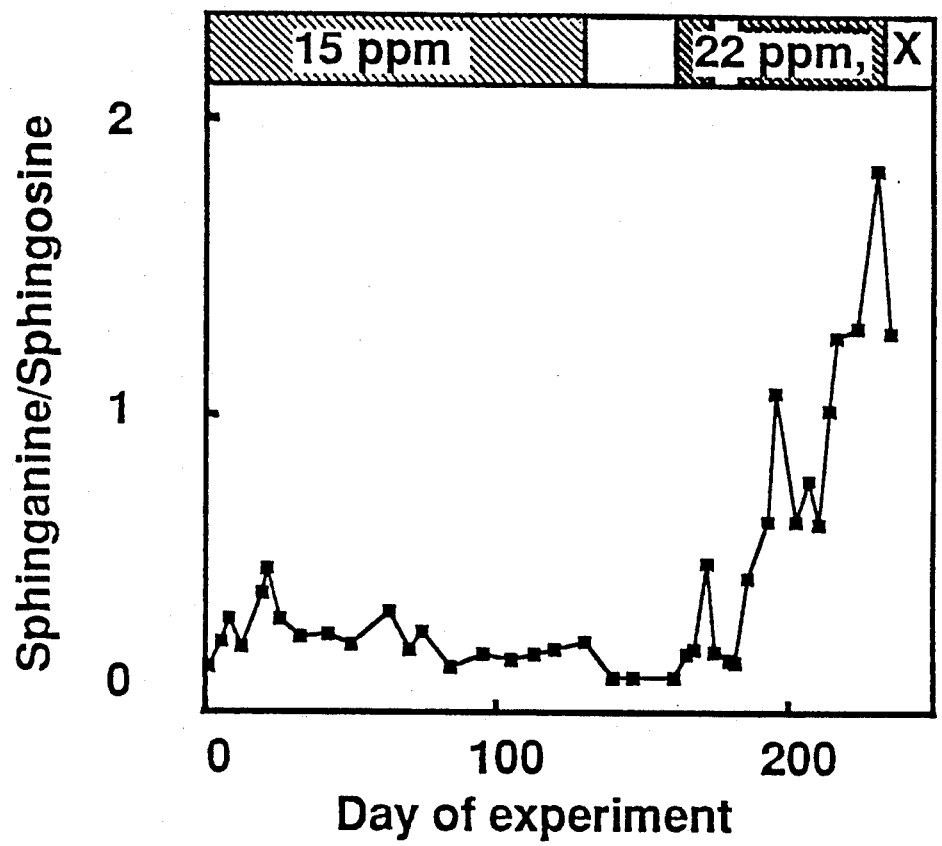
Figure 8C:
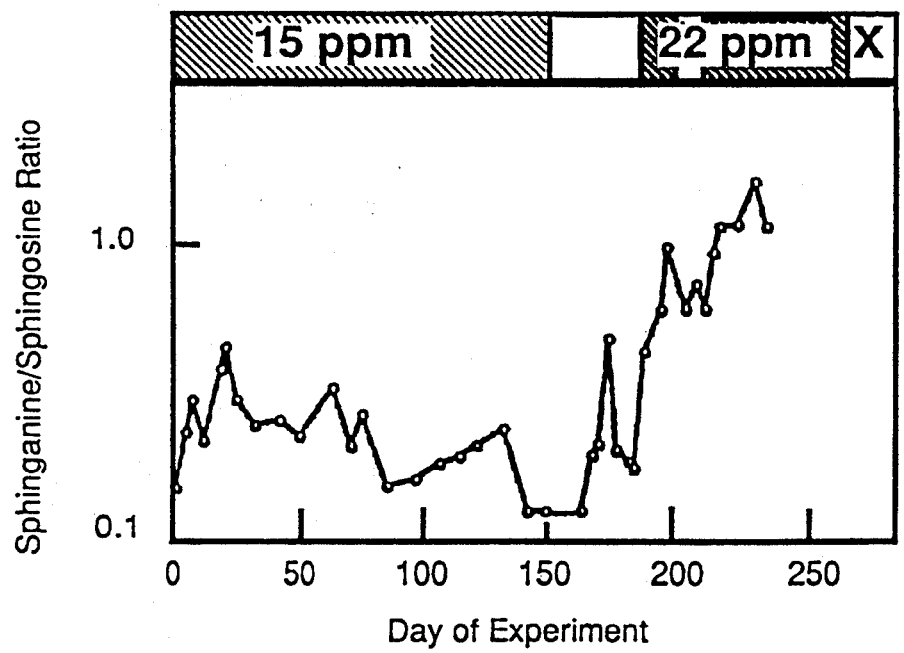

The fourth pony (#341) was given lower amounts of fumonisin-contaminated feed as shown in FIG. 8. During the first 130 days at 15 ppm fumonisin B1, the levels of free sphingosine and sphinganine fluctuated with no noticeable pattern (data not shown); however, when the data are expressed as the ratio of these compounds, there was a fairly consistent elevation over the initial value. Although the initial ratio is based on a single serum sample at the start of the experiment, it was similar to that of the other animals studied.

When pony 341 was taken off the fumonisin between day 130 and 160, the ratio dropped to a level that was below the starting level. Fumonisin feeding was resumed at 22 ppm on day 161, and there was a rapid increase in the sphinganine to sphingosine ratio, and the radio declined again when the pony was taken off fumonisin between days 175 and 182. Reintroduction of 22 ppm fumonisin B1 on day 182 was accomplished by a rapid increase in the ratio to >1.5, which culminated in a precipitous fall on day 235. Later that day the pony died with the symptoms of equine leucoencephalomalacia, which was later confirmed by biopsy. This final decrease in the ratio was due to a greater than two-fold increase in sphingosine (i.e., from 163 to 418 pmol/ml between day 231 and 235, rather than to a reduction in sphinganine (which also increased from 256 to 532 pmol/ml.

The upper panel of FIG. 8 shows serum AST/SGOT of pony 341 over this period. The activities were essentially unaffected until between day 224 and 231. Other markers of liver function were also unaltered until this period. Thus, changes in the free long-chain bases appeared much earlier (at least a month or more) before exposure to fumonisins was detectable by elevations in liver enzymes.

If the elevation in sphinganine is due to inhibition of de novo sphingolipid biosynthesis, this might also be reflected in a reduction in the amounts of examined with sera from several of the ponies as shown in Table 6.

TABLE 6

Levels of long-chain bases liberated from the total serum lipids upon acid hydrolysis to cleave more complex sphingolipids

| Day of Trial | Sphingosine pmol/ml Total (-free) | Sphinganine pmol/ml Total (-free) | AST/ SGOT units |
|---|---|---|---|
| Pony 164 | | | |
| −20 | 3400 ± 266 (ND) | 203 ± 18 (ND) | 270 |
| −15 | 2670 ± 678 (2630) | 139 ± 22 (127) | 224 |
| 2 | 621 ± 99 (504) | 169 ± 30 (99) | 235 |
| 7 | 254 ± 32 (102) | 156 ± 48 (0)[2] | 357 |
| 10 | 2960 ± 585 (2740) | 786 ± 234 (503) | 4000 |
| Pony 166 | | | |
| −22 | 3620 ± 452 (3580) | 123 ± 23 (103) | 215 |
| −15 | 4430 ± 409 (4380) | 93 ± 9 (70) | 180 |
| −1 | 2340 ± 694 (2290) | 211 ± 69 (197) | 210 |

TABLE 6-continued

Levels of long-chain bases liberated from the total serum lipids upon acid hydrolysis to cleave more complex sphingolipids

| Day of Trial | Sphingosine pmol/ml Total (-free) | Sphinganine pmol/ml Total (-free) | AST/ SGOT units |
|---|---|---|---|
| 2 | 1020 ± 313 (974) | 131 ± 40 (94) | 199 |
| 7 | 950 ± 154 (985) | 206 ± 18 (144) | 215 |
| 10 | 634 ± 192 (540) | 212 ± 28 (34) | 1470 |
| 13 | 1740 ± 150 (1640) | 823 ± 54 (650) | 2080 |
| Pony 208 | | | |
| −22 | 6940 ± 88 (6610) | 267 ± 11 (235) | 419 |
| −15 | 4950 ± 163 (4750) | 178 ± 3 (153) | 327 |
| −1 | 5540 ± 42 (5270) | 218 ± 18 (279) | 305 |
| 2 | 3490 ± 358 (3190) | 387 ± 26 (107) | 344 |
| 6 | 2390 ± 388 (2030) | 718 ± 75 (60) | 2130 |
| 10 | 4450 ± 10 (3460) | 2040 ± 70 (200) | 1240 |
| 13 | 15970 ± 1576 (15040) | 9990 ± 379 (9604) | 1010 |

[1] The description of the ponies is given in the text and Table 3. Data is not given for a few of the days of feeding because there was too little sample available to conduct the analysis.
[2] These values underestimate the contribution of free long-chain bases because they are somewhat unstable under the acid hydrolysis conditions.

For these analyses, the lipids were extracted and then hydrolyzed to liberate the free long-chain bases which were analyzed by HPLC. The results (Table 6) show that the levels of total (complex) sphingolipids were reduced by 50 to 95% during the early times after feeding fumonisin, but that the levels increased again when there was also an elevation in hepatic enzymes. As discussed earlier, this increase may reflect the release of membrane sphingolipids into circulation upon cell injury.

Since pony 164 was clearly undergoing rapid tissue injury (as reflected in the marked elevation in sphingosine was due to the turnover of sphingolipids in injured tissues. This is, again, consistent with a mechanism whereby a block at the level of acylation of newly synthesized sphinganine occurs as described above. That study showed that inhibition of ceramide synthase results in accumulation of sphinganine as an intermediate of de novo sphingolipid biosynthesis. The free sphingosine (and some sphinganine) occurs from the turnover of existing complex sphingolipids; hence, this will be affected somewhat as fumonisins inhibit the reacylation of this long-chain base. In both the magnitude and the speed with which changes appeared, the increase in serum long-chain bases was an earlier indicator of exposure to fumonisins than elevations in AST/SGOT for both of these ponies. Hence, changes in the sphinganine to sphingosine ratio can detect exposure of ponies to fumonisin by 1 to 2 months earlier than liver function tests.

Synthesis of Fumonisin and Fumonisin Analogs

The following more particularly describes the synthesis of fumonisin and fumonisin analogs (see FIG. 1), which are intended as illustrative only since numerous modifications and variations therein will be apparent to those skilled in the art. Numeral references following a particular compound refer to the structures found in FIG. 9.

The synthesis of the fumonisin analog 2-aminooctadeca-3,5-diol from L-alanine methyl ester hydrochloride (1) is given below. Obviously, a particular fumonisin or other fumonisin analogs can be formed utilizing this general synthesis by the addition of the appropriate Grignard reagent to compound 4 and, if necessary, functionalization of oxygen or nitrogen atoms contained in that Grignard reagent at the appropriate time to attach mono- or polycarboxylate moieties to the tail of the compound. Ester or ceramide couplings of this type can be readily accomplished using a variety of reagents well-known to those skilled in the art. Furthermore, the X and Y substituents, as shown in the fumonisin analog of FIG. 1, can be added by methods known in the art. introduction of the V-substituent can be readily accomplished using a hydride opening of an epoxide (e.g., 6 of FIG. 9) to obtain V=H) or an epoxide opening with a variety of oxygen nucleophiles to ultimately obtain V=OH. By controlling both the stereochemistry of the epoxidation (e.g., 5a→6 of FIG. 9) and the regiochemistry of the subsequent epoxide opening with hydride or oxygen nucleophiles, the preparation of all possible variations of V and Y=H or OH can be achieved. Because the head group is likely to be an important factor in modulating the biological activity of the compound in question, modifications of this type may prove to be important.

L-Alanine methyl ester hydrochloride (1) (1.0 eq, 179.1 mmol, 25 gm) was dissolved in 500 ml of dry N, N-dimethylformamide (DMF) under a nitrogen atmosphere. Distilled triethylamine (2.5 eq, 447.2 mmol, 45.3 gm) and di-t-butyl dicarbonate ($(BOC)_2O$) (1.1 eq, 197.4 mmol, 43 gm) were then added and the reaction mixture was heated and stirred at 60° C. for 1 hour and at room temperature for an additional 4 hours. The DMF was then evaporated in vacuo and the remaining residue was dissolved in ethyl acetate, cooled to 5° C., washed with 10% citric acid, saturated $NaHCO_3$, and brine, dried over anhydrous $MgSO_4$, filtered, and the solvent was evaporated in vacuo. The N-BOC-protected ester 2 was purified via flash column chromatography and a colorless oil was obtained in 88% yield.

Ester 2 (1.0 eq, 49.3 mmol, 10 gm) was dissolved in dry toluene (400 ml) and cooled to −78° C. under a nitrogen atmosphere. Diisobutylaluminum hydride (DIBAL-H) (1.4 eq, 69.0 mmol) was then added slowly and the reaction monitored by TLC. After 3.5 hours, the reaction was quenched at −78° C. with ethanol and allowed to warm to room temperature. The turbid solution was filtered through silica gel and the aluminum salts were thoroughly washed with ether. Rotary evaporation of the solvent yielded the product (3) (82% yield) as a white solid and the aldehyde was purified by flash column chromatography.

Aldehyde 3 (1.0 eq, 17.9 mmol, 3.1 gm) and triphenylphosphoranylidine acetaldehyde (2.2 eq, 39.4 mmol, 12.1 gm) were dissolved in 250 ml of dry benzene and refluxed under a nitrogen atmosphere for 2 hours. Benzene was evaporated in vacuo and the crude product (brown solid) was purified via flash column chromatography. The unsaturated aldehyde 4 was isolated in 72% yield and used immediately.

An excess of magnesium turnings was placed in a 3-neck round bottom flask and flame-dried under a vacuum. After cooling, 125 ml of ether was added followed by 1-bromotridecane (2.2 eq, 28.8 mmol, 7.6 gm) and the mixture was stirred under reflux for 24 hours. Aldehyde 4 (1.0 eq, 13.1 mmol, 2.6 gm) was dissolved in 100 ml of ether under a nitrogen atmosphere and cooled to 0° C. The Grignard reagent was then cannulated into the aldehyde solution and allowed to warm up to room temperature for 2 hours. The reaction was then quenched with saturated $NH_4Cl$ solution and the organic layer was washed with brine, dried over $MgSO_4$, and concentrated in vacuo. The diasteriomeric mixture of alcohols (5) were separated via flash column chromatography and isolated in 86% yield.

Allylic alcohol 5a (1.0 eq, 0.63 mmol, 240 mg) was dissolved in 10 ml $CHCl_2$ and 10 ml of 0.5M $NaHCO_3$. meta-Chloroperbenzoic acid (1.1 eq, 0.69 mmol, 120 mg) was added slowly and the reaction was stirred overnight. The organic layer was then washed with brine, dried over $MgSO_4$ and concentrated in vacuo. The mixture of diasteriomeric epoxides (6) were separated by flash column chromatography in 90% yield.

Epoxide 6a (1.0 eq, 72.5 mmol, 30 mg) was dissolved in 5 ml of dry THF and cooled to 0° C. under a nitrogen atmosphere. Bis(2-methoxyethoxy)aluminum hydride (2.5 eq, 0.19 mmol) was then added and the reaction mixture was allowed to warm up overnight. The reaction was quenched with ethanol, filtered over celite and concentrated in vacuo to produce diol 7 in 76% yield after purification. Sodium triacetoxyborohydride can also be utilized to produce diol 7 at this step.

Carbamate 7 (1.0 eq, 124 mmol, 50 mg) was dissolved in 25 ml of ethyl acetate and cooled to 0° C. under a nitrogen atmosphere. Dry HCL gas (>3 eq) was bubbled through the solution and allowed to stir for 6 hours at 0° C. as determined by TLC. The reaction was then basified to pH 9 with 10% $NH_4OH$ and the organic layer washed with brine, dried over anhydrous $MgSO_4$, and concentrated in vacuo. Flash column chromatography produced the amino diol 8 as a white solid in 78% yield.

With reference to the definition of fumonisin analogs given above, the Spacer Groups can be added to the various head groups in two different fashions. The first involves a Wittig (or Wadsworth/Emmons/Horner) olefination in which an ylide containing a terminal oxygen, nitrogen or carboxyl functional group is allowed to react with an aldehyde. Examples of the types of ylides used are given by the structure:

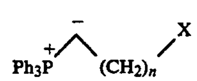

where n=1-20 (straight or branched chain and X=O-Protecting Group, NH-Protecting Group, NR-Protecting Group, $CO_2H$ (Li).

The second approach involves an acetylide addition to an aldehyde. The types of acetylides which are used are shown below:

$M\equiv(CH_2)_n-X$ where n=1-20 (straight or branched chain; X=O-Protecting Group, NH-Protecting Group, NR-Protecting Group (wherein R=a straight or branched chain $C_1$-$C_6$ alkyl), $CO_2H(M)$; and M=Li, Na, K, etc. As used herein, "a Protecting group" refers to a moiety that provides protection for the corresponding alcohol or amide until deprotection is desired. This protection/-deprotection process is well-known in the art as discussed in (41).

FIG. 10 shows various reaction schemes that can be employed to control the stereochemistry of the 2-aminopenta-3,5-diol head group during the synthesis of a fumonisin or fumonisin analog. FIG. 11 shows various reaction schemes that can be employed to control the stereochemistry of the aminotriol head groups present in Alternaria toxins or fumonisin analogs similar to Alternaria toxins.

Although the present processes have been described with reference to specific details of certain embodiments thereof, it is not intended that such details should be regarded as limitations upon the scope of the invention except as and to the extent that they are included in the accompanying claims.

REFERENCES

1. Marasas, W. F. O., Nelson, P. E., and Toussoun, T. A, *Toxigenic Fusarium Species: Identity and Mycotoxicology*. The Pennsylvania State University Press, University Park, Pa. (1984).

2. Kellerman, T. S., Marasas, W. F. O., Pienaar, J. G., and Naude, T. W. (1972) *Onderstepoort J. Vet. Res.* 39, 205-208.

3. Kriek, N. P. J., Kellerman, T. S., and Marasas, W. F. O. (1981) *Onderstepoort J. Vet. Res.* 55, 129-131.

4. Marasas, W. F. O., Kriek, N. P. J., Fincham, J. E. and van Rensburg, S. J. (1984) *Int. J. Cancer* 34, 383-387.

5. K. A. Voss, R. D. Plattner, C. W. Bacon, and W. P. Norre (1990) *Mycopathologia* 112, 81-92.

6. Marasas, W. F. O. (1982) in *Cancer of the Oesophagus*, Vol. 1, (Pfeiffer, C. J., ed.) CRC Press, Boca Raton, pp. 29-40.

7. Lin, M., Lu, S., Ji, C., Wang, Y., Wang, M., Cheng, S., and Tian, G. (1980) in *Genetic and Environmental Factors in Experimental and Human Cancer* (Gelboin, H. V., ed.) *Japan Sci. Soc. Press*, Tokyo, pp. 139-148.

8. Yang, C. S. (1980) *Cancer Res.* 40, 2633-2644.

9. Bezuidehout, C. S., Gelderblom, W. C. A., Gorstallman, C. P., Horak, R. M., Marasas, W. F. O., Spiteller, G., and Vleggaar, R. (1988) *J. Chem. Soc. Comm.* 743-745.

10. Voss, K. A., Norred, W. P., Plattner, R. D., and Bacon, C. W. (1989) *Food Chem. Toxicol.* 27, 89-96.

11. Sydenham, E. W., Gelderblom, W. C. A., Thiel, P. G., and Marasas, W. F. O. (1990) *J. Agric. Food Chem.* 38, 285-290.

12. Marasas, W. F. O., Kellerman, T. S., Gelderblom, W. C. A., Coetzer, J. A. W., Thiel, P. G., and van der Lugt, J. J. (1988) *Onderstepoort J. Vet. Res.* 55, 197-203.

13. Harrison, L. R., Colvin, B., Greene, J. T., Newman, L. E., and Cole, J. R. (1990) *J. Vet. Diagn. Invest.* 2, 217-221.

14. Gelderblom, W. C. A., Jaskiewicz, K., Marasas, W. F. O., Thiel, P. G., Horak, R. M., Vleggaar, R., and Kriek, N. P. J. (1988) *Appl. Environ. Microbiol.* 54, 1806-1811.

15. Ross, P. F., Rice, L. G., Plattner, R. D., Osweiler, G. D., Wilson, T. M., Owens, D. L., Nelson, H. A. and Richard, J. L. (1991) *Mycopathologia* (in press)

16. Hakomori, S.-I. (1981) *Ann. Rev. Biochem.* 50, 733-764.

17. Sweeley, C. C. (1985) In *Biochemistry of Lipids and Membranes* (D. E. Vance and J. E. Vance, eds.) Benjamin/Cummings Pub., Menlo Park, Calif., Chapter 12.

18. Hannun, Y. A. and Bell, R. M. (1989) *Science* 243, 500-507.

19. Hakomori, S.-I. (1990) *J. Biol. Chem.* 265, 18713-18716.

20. Merrill, A. H., Jr. (1991) *J. Bioenerget.* 23, 83-104.

21. Merrill, A. H., Jr., Nimkar, S., Menaldino, D., Hannun, Y. S., Loomis, C., Bell, R. M., Tyagi, S. R., Lambeth, J. D., Stevens, V. L., Hunter, R., and Liotta, D. C. (1989) *Biochemistry* 28, 4360-4366.

22. Yao, Z. and Vance, D. E., (1988) *J. Biol. Chem.* 263, 2998–3004.

23. Merrill, A. H., Jr. and Wang, E. (1986) *J. Biol. Chem.* 261, 3764–3769.

24. Messmer, T. O., Wang, E., Stevens, V. L., and Merrill, A. H., Jr. (1989) *J. Nutr.* 119, 534–538.

25. Gaver, R. and Sweeley, C. C. (1966) *J. Amer. Chem. Soc.* 88, 3643–3647.

26. Medlock, K. A. and Merrill, A. H., Jr. (1988) *Biochem. Biophys. Res. Commun.* 157, 232–237.

27. Slife, C. W., Wang, E., Hunter, R., Wang, S., Burgess, C., Liotta, D. C., and Merrill, A. H. Jr. (1989) *J. Biol. Chem.* 264, 10371–10377.

28. Merrill, A. H., Jr., Wang, E. Mullins, R. E., Jamison, W. C. L., Nimkar, S., and Liotta, D. C. (1988) *Anal. Biochem.* 171, 373–381.

29. Williams, R. D., wang, E., and Merrill, A. H., Jr. (1984) *Arch. Biochem. Biophys.* 228, 282–291.

30. Morrell, P. and Radin, N. S. (1970) *J. Biol. Chem.* 245, 342–350.

31. Jaskiewicz, K., van Rensburg, S. J., Marasas, W. F., and Gelderblom, W. C. (1987) *J. Natl. Cancer Inst.* 78, 321–325.

32. Merrill, A. H., Jr. and Jones, D. D. (1990) *Biochem. Biophys. Acta* 1044, 1–12.

33. Bottini, A. T., Bowen, J. R., and Gilchrist, D. G. (1981) *Tetrahedron Lett.* 22, 2723–2726.

34. Merrill, A. H., Jr. (1983) *Biochem. Biophys. Acta* 754, 284–291.

35. Stevens, V. L., Nimkar, S., Jamison, W. C., Liotta, D. C., and Merrill, A. H., Jr. (1990) *Biochem. Biophys. Acta* 1051, 37–45.

36. Zhang, H., Buckley, N. E., Gibson, K., and Spiegel, S. (1990) *J. Biol. Chem.* 265, 76–81.

37. Hannun, Y. A., Loomis, C. R., Merrill, A. H., Jr. and Bell, R. M. (1986) *J. Biol. Chem.* 261, 12604–12609.

38. Faucher, M., Girones, N., Hannun, Y. A., Bell, R. M., and Davis, R. J. (1988) *J. Biol. Chem.* 263, 5319–5327.

39. Oishi, K., Zheng, B. and Kuo, J.-F. (1990) *J. Biol. Chem.* 265, 70–75.

40. Jamal, Z., Martin, A., Gomez-Munoz, A. and Brindley, D. N. (1991) *J. Biol. Chem.* 266, 2988–2996.

41. Greene, T. W., *Protecting Groups in Organic Chemistry*, John Wiley and Sons, NYC, 1981.

What is claimed is:

1. A method of detecting the consumption of a fumonisin, or an analog thereof, in a subject comprising detecting, in a sample from the subject, the presence of inhibition of ceramide synthease, the presence of the inhibition of ceramide synthase indicating the consumption of a fumonisin or fumonisin analog.

2. The method of claim 1, wherein the inhibition of ceramide synthase is detected by detecting an increase in sphinganine in the sample from the subject.

3. The method of claim 1, wherein the inhibition of ceramide synthase is detected by detecting a decrease in ceramide in the sample from the subject.

4. The method of claim 1, wherein the inhibition of ceramide synthase is detected by detecting an increase in the amount of sphinganine relative to the amount of sphingosine in the sample from the subject.

5. The method of claim 1, wherein the fumonisin is fumonisin $B_1$.

6. The method of claim 1, wherein the fumonisin is fumonisin $B_2$.

7. The method of claim 1, wherein the fumonisin analog is an Alternaria toxin.

8. The method of claim 1, wherein the subject is a human.

9. The method of claim 1, wherein the subject is a horse.

* * * * *